(12) United States Patent
Yun et al.

(10) Patent No.: US 10,578,566 B2
(45) Date of Patent: Mar. 3, 2020

(54) X-RAY EMISSION SPECTROMETER SYSTEM

(71) Applicant: Sigray, Inc., Concord, CA (US)

(72) Inventors: Wenbing Yun, Walnut Creek, CA (US); Srivatsan Seshadri, Pleasanton, CA (US); Sylvia Jia Yun Lewis, San Francisco, CA (US); Janos Kirz, Berkeley, CA (US)

(73) Assignee: Sigray, Inc., Concord, CA (US)

( * ) Notice: Subject to any disclaimer, the term of this patent is extended or adjusted under 35 U.S.C. 154(b) by 0 days.

(21) Appl. No.: 16/371,606

(22) Filed: Apr. 1, 2019

(65) Prior Publication Data

US 2019/0302042 A1 Oct. 3, 2019

Related U.S. Application Data

(60) Provisional application No. 62/651,883, filed on Apr. 3, 2018.

(51) Int. Cl.
*G01N 23/223* (2006.01)
*G01N 23/22* (2018.01)
(Continued)

(52) U.S. Cl.
CPC ....... *G01N 23/2209* (2018.02); *G01N 23/223* (2013.01); *G01N 23/2204* (2013.01); *G01N 2223/501* (2013.01)

(58) Field of Classification Search
CPC ......... G01N 2223/501; G01N 23/2204; G01N 23/2209; G01N 23/223
See application file for complete search history.

(56) References Cited

U.S. PATENT DOCUMENTS

| 1,203,495 A | 10/1916 | Coolidge |
| 1,211,092 A | 1/1917 | Coolidge |

(Continued)

FOREIGN PATENT DOCUMENTS

| CN | 102124537 A | 7/2011 |
| CN | 102551761 A | 7/2012 |

(Continued)

OTHER PUBLICATIONS

"Diamond," Section 10.4.2 of Zorman et al., "Material Aspects of Micro-Nanoelectromechanical Systems," Chapter 10 of Springer Handbook of Nanotechnology, 2nd ed., Barat Bushan, ed. (Springer Science + Business Media, Inc., New York, 2007), pp. 312-314.

(Continued)

*Primary Examiner* — Mark R Gaworecki
(74) *Attorney, Agent, or Firm* — Knobbe, Martens, Olson & Bear LLP

(57) ABSTRACT

Systems and methods for x-ray emission spectroscopy are provided in which at least one x-ray analyzer is curved and receives and diffracts fluorescence x-rays emitted from a sample, and at least one spatially-resolving x-ray detector receives the diffracted x-rays. The at least one x-ray analyzer and the at least one spatially-resolving x-ray detector are positioned on the Rowland circle. In some configurations, the fluorescence x-rays are emitted from the same surface of the sample that is irradiated by the x-rays from an x-ray source and the system has an off-Rowland circle geometry. In some other configurations, an x-ray optical train receives the fluorescence x-rays emitted from a sample impinged by electrons within an electron microscope and focuses at least some of the received fluorescence x-rays to a focal spot.

22 Claims, 18 Drawing Sheets

(51) Int. Cl.
*G01N 23/2209* (2018.01)
*G01N 23/2204* (2018.01)

(56) References Cited

U.S. PATENT DOCUMENTS

| | | | |
|---|---|---|---|
| 1,215,116 A | 2/1917 | Coolidge |
| 1,328,495 A | 1/1920 | Coolidge |
| 1,355,126 A | 10/1920 | Coolidge |
| 1,790,073 A | 1/1931 | Pohl |
| 1,917,099 A | 7/1933 | Coolidge |
| 1,946,312 A | 2/1934 | Coolidge |
| 2,926,270 A | 2/1960 | Zunick |
| 3,795,832 A | 3/1974 | Holland |
| 4,165,472 A | 8/1979 | Wittry |
| 4,227,112 A | 10/1980 | Waugh et al. |
| 4,266,138 A | 5/1981 | Nelson et al. |
| 4,426,718 A | 1/1984 | Hayashi |
| 4,523,327 A | 6/1985 | Eversole |
| 4,573,186 A | 2/1986 | Reinhold |
| 4,807,268 A | 2/1989 | Wittrey |
| 4,940,319 A | 7/1990 | Ueda et al. |
| 4,951,304 A | 8/1990 | Piestrup et al. |
| 4,972,449 A | 11/1990 | Upadhya et al. |
| 5,001,737 A | 3/1991 | Lewis et al. |
| 5,008,918 A | 4/1991 | Lee et al. |
| 5,132,997 A | 7/1992 | Kojima |
| 5,148,462 A | 9/1992 | Spitsyn et al. |
| 5,173,928 A | 12/1992 | Momose et al. |
| 5,249,216 A | 9/1993 | Ohsugi et al. |
| 5,276,724 A | 1/1994 | Kumasaka et al. |
| 5,602,899 A | 2/1997 | Larson |
| 5,604,782 A | 2/1997 | Cash, Jr. |
| 5,629,969 A | 5/1997 | Koshishiba |
| 5,657,365 A | 8/1997 | Yamamoto et al. |
| 5,682,415 A | 10/1997 | O'Hara |
| 5,715,291 A | 2/1998 | Momose |
| 5,729,583 A | 3/1998 | Tang et al. |
| 5,737,387 A | 4/1998 | Smither |
| 5,768,339 A | 6/1998 | O'Hara |
| 5,772,903 A | 6/1998 | Hirsch |
| 5,778,039 A | 7/1998 | Hossain |
| 5,812,629 A | 9/1998 | Clauser |
| 5,825,848 A | 10/1998 | Virshup et al. |
| 5,832,052 A | 11/1998 | Hirose et al. |
| 5,857,008 A | 1/1999 | Reinhold |
| 5,878,110 A | 3/1999 | Yamamoto et al. |
| 5,881,126 A | 3/1999 | Momose |
| 5,912,940 A | 6/1999 | O'Hara |
| 5,930,325 A | 7/1999 | Momose |
| 6,108,397 A | 8/2000 | Cash, Jr. |
| 6,108,398 A | 8/2000 | Mazor et al. |
| 6,118,853 A | 9/2000 | Hansen et al. |
| 6,125,167 A | 9/2000 | Morgan |
| 6,278,764 B1 | 8/2001 | Barbee, Jr. et al. |
| 6,307,916 B1 | 10/2001 | Rogers et al. |
| 6,359,964 B1 | 3/2002 | Kogan |
| 6,377,660 B1 | 4/2002 | Ukita et al. |
| 6,381,303 B1 | 4/2002 | Vu et al. |
| 6,389,100 B1 | 5/2002 | Verman et al. |
| 6,430,254 B2 | 8/2002 | Wilkins |
| 6,442,231 B1 | 8/2002 | O'Hara |
| 6,456,688 B1 | 9/2002 | Taguchi et al. |
| 6,463,123 B1 | 10/2002 | Korenev |
| 6,487,272 B1 | 11/2002 | Kutsuzawa |
| 6,504,902 B2 | 1/2003 | Iwasaki et al. |
| 6,507,388 B2 | 1/2003 | Burghoorn |
| 6,553,096 B1 | 4/2003 | Zhou et al. |
| 6,560,313 B1 | 5/2003 | Harding et al. |
| 6,560,315 B1 | 5/2003 | Price et al. |
| 6,707,883 B1 | 3/2004 | Tiearney et al. |
| 6,711,234 B1 | 3/2004 | Loxley et al. |
| 6,811,612 B2 | 11/2004 | Gruen et al. |
| 6,815,363 B2 | 11/2004 | Yun et al. |
| 6,829,327 B1 | 12/2004 | Chen |
| 6,847,699 B2 | 1/2005 | Rigali et al. |
| 6,850,598 B1 | 2/2005 | Fryda et al. |
| 6,870,172 B1 | 3/2005 | Mankos et al. |
| 6,885,503 B2 | 4/2005 | Yun et al. |
| 6,914,723 B2 | 7/2005 | Yun et al. |
| 6,917,472 B1 | 7/2005 | Yun et al. |
| 6,947,522 B2 | 9/2005 | Wilson et al. |
| 6,975,703 B2 | 12/2005 | Wilson et al. |
| 7,003,077 B2 | 2/2006 | Jen et al. |
| 7,006,596 B1 | 2/2006 | Janik |
| 7,015,467 B2 | 3/2006 | Maldonado et al. |
| 7,023,955 B2 | 4/2006 | Chen et al. |
| 7,057,187 B1 | 6/2006 | Yun et al. |
| 7,079,625 B2 | 7/2006 | Lenz |
| 7,095,822 B1 | 8/2006 | Yun |
| 7,110,503 B1 | 9/2006 | Kumakhov |
| 7,119,953 B2 | 10/2006 | Yun et al. |
| 7,130,375 B1 | 10/2006 | Yun et al. |
| 7,170,969 B1 | 1/2007 | Yun et al. |
| 7,180,979 B2 | 2/2007 | Momose |
| 7,180,981 B2 | 2/2007 | Wang |
| 7,183,547 B2 | 2/2007 | Yun et al. |
| 7,215,736 B1 | 5/2007 | Wang et al. |
| 7,215,741 B2 | 5/2007 | Ukita et al. |
| 7,218,700 B2 | 5/2007 | Huber et al. |
| 7,218,703 B2 | 5/2007 | Yada et al. |
| 7,221,731 B2 | 5/2007 | Yada et al. |
| 7,245,696 B2 | 7/2007 | Yun et al. |
| 7,268,945 B2 | 9/2007 | Yun et al. |
| 7,286,640 B2 | 10/2007 | Yun et al. |
| 7,297,959 B2 | 11/2007 | Yun et al. |
| 7,298,826 B2 | 11/2007 | Inazuru |
| 7,330,533 B2 | 2/2008 | Sampayon |
| 7,346,148 B2 | 3/2008 | Ukita |
| 7,346,204 B2 | 3/2008 | Ito |
| 7,349,525 B2 | 3/2008 | Morton |
| 7,359,487 B1 | 4/2008 | Newcome |
| 7,365,909 B2 | 4/2008 | Yun et al. |
| 7,365,918 B1 | 4/2008 | Yun et al. |
| 7,382,864 B2 | 6/2008 | Hebert et al. |
| 7,388,942 B2 | 6/2008 | Wang et al. |
| 7,394,890 B1 | 7/2008 | Wang et al. |
| 7,400,704 B1 | 7/2008 | Yun et al. |
| 7,406,151 B1 | 7/2008 | Yun |
| 7,412,024 B1 | 8/2008 | Yun et al. |
| 7,412,030 B1 | 8/2008 | O'Hara |
| 7,412,131 B2 | 8/2008 | Lee et al. |
| 7,414,787 B2 | 8/2008 | Yun et al. |
| 7,433,444 B2 | 10/2008 | Baumann |
| 7,440,542 B2 | 10/2008 | Baumann |
| 7,443,953 B1 | 10/2008 | Yun et al. |
| 7,453,981 B2 | 11/2008 | Baumann |
| 7,463,712 B2 | 12/2008 | Zhu et al. |
| 7,486,770 B2 | 2/2009 | Baumann |
| 7,492,871 B2 | 2/2009 | Popescu |
| 7,499,521 B2 | 3/2009 | Wang et al. |
| 7,515,684 B2 | 4/2009 | Gibson et al. |
| 7,522,698 B2 | 4/2009 | Popescu |
| 7,522,707 B2 | 4/2009 | Steinlage et al. |
| 7,522,708 B2 | 4/2009 | Heismann |
| 7,529,343 B2 | 5/2009 | Safai et al. |
| 7,532,704 B2 | 5/2009 | Hempel |
| 7,551,719 B2 | 6/2009 | Yokhin et al. |
| 7,551,722 B2 | 6/2009 | Ohshima et al. |
| 7,561,662 B2 | 7/2009 | Wang et al. |
| 7,564,941 B2 | 7/2009 | Baumann |
| 7,583,789 B1 | 9/2009 | Macdonald et al. |
| 7,601,399 B2 | 10/2009 | Barnola et al. |
| 7,639,786 B2 | 12/2009 | Baumann |
| 7,646,843 B2 | 1/2010 | Popescu et al. |
| 7,672,433 B2 | 3/2010 | Zhong et al. |
| 7,680,243 B2 | 3/2010 | Yokhin et al. |
| 7,787,588 B1 | 8/2010 | Yun et al. |
| 7,796,725 B1 | 9/2010 | Yun et al. |
| 7,796,726 B1 | 9/2010 | Gendreau et al. |
| 7,800,072 B2 | 9/2010 | Yun et al. |
| 7,809,113 B2 | 10/2010 | Aoki et al. |
| 7,813,475 B1 | 10/2010 | Wu et al. |
| 7,817,777 B2 | 10/2010 | Baumann et al. |
| 7,864,426 B2 | 1/2011 | Yun et al. |

(56) References Cited

U.S. PATENT DOCUMENTS

| | | |
|---|---|---|
| 7,864,922 B2 | 1/2011 | Kawabe |
| 7,873,146 B2 | 1/2011 | Okunuki et al. |
| 7,876,883 B2 | 1/2011 | O'Hara |
| 7,889,838 B2 | 2/2011 | David et al. |
| 7,889,844 B2 | 2/2011 | Okunuki et al. |
| 7,914,693 B2 | 3/2011 | Jeong et al. |
| 7,920,673 B2 | 4/2011 | Lanza et al. |
| 7,920,676 B2 | 4/2011 | Yun et al. |
| 7,924,973 B2 | 4/2011 | Kottler et al. |
| 7,929,667 B1 | 4/2011 | Zhuang et al. |
| 7,945,018 B2 | 5/2011 | Heismann |
| 7,949,092 B2 | 5/2011 | Brons |
| 7,949,095 B2 | 5/2011 | Ning |
| 7,974,379 B1 | 7/2011 | Case et al. |
| 7,983,381 B2 | 7/2011 | David et al. |
| 7,991,120 B2 | 8/2011 | Okunuki et al. |
| 8,005,185 B2 | 8/2011 | Popescu |
| 8,009,796 B2 | 8/2011 | Popescu |
| 8,009,797 B2 | 8/2011 | Ouchi |
| 8,041,004 B2 | 10/2011 | David |
| 8,036,341 B2 | 11/2011 | Lee |
| 8,058,621 B2 | 11/2011 | Kommareddy |
| 8,068,579 B1 | 11/2011 | Yun et al. |
| 8,073,099 B2 | 12/2011 | Niu et al. |
| 8,094,784 B2 | 1/2012 | Morton |
| 8,139,711 B2 | 3/2012 | Takahashi |
| 8,139,716 B2 | 3/2012 | Okunuki et al. |
| 8,184,771 B2 | 5/2012 | Murakoshi |
| 8,208,602 B2 | 6/2012 | Lee |
| 8,208,603 B2 | 6/2012 | Sato |
| 8,233,587 B2 | 7/2012 | Sato |
| 8,243,879 B2 | 8/2012 | Itoh et al. |
| 8,243,884 B2 | 8/2012 | Rödhammer et al. |
| 8,280,000 B2 | 10/2012 | Takahashi |
| 8,306,183 B2 | 11/2012 | Koehler |
| 8,306,184 B2 | 11/2012 | Chang et al. |
| 8,351,569 B2 | 1/2013 | Baker |
| 8,351,570 B2 | 1/2013 | Nakamura |
| 8,353,628 B1 | 1/2013 | Yun et al. |
| 8,360,640 B2 | 1/2013 | Reinhold |
| 8,374,309 B2 | 2/2013 | Donath |
| 8,406,378 B2 | 3/2013 | Wang et al. |
| 8,416,920 B2 | 4/2013 | Okumura et al. |
| 8,422,633 B2 | 4/2013 | Lantz et al. |
| 8,451,975 B2 | 5/2013 | Tada |
| 8,422,637 B2 | 6/2013 | Okunuki et al. |
| 8,509,386 B2 | 8/2013 | Lee et al. |
| 8,520,803 B2 | 8/2013 | Behling |
| 8,526,575 B1 | 9/2013 | Yun et al. |
| 8,532,257 B2 | 9/2013 | Mukaide et al. |
| 8,553,843 B2 | 10/2013 | Drory |
| 8,559,594 B2 | 10/2013 | Ouchi |
| 8,559,597 B2 | 10/2013 | Chen et al. |
| 8,565,371 B2 | 10/2013 | Bredno |
| 8,576,983 B2 | 11/2013 | Baeumer |
| 8,591,108 B2 | 11/2013 | Tada |
| 8,602,648 B1 | 12/2013 | Jacobsen et al. |
| 8,632,247 B2 | 1/2014 | Ishii |
| 8,666,024 B2 | 3/2014 | Okunuki et al. |
| 8,666,025 B2 | 3/2014 | Klausz |
| 8,699,667 B2 | 4/2014 | Steinlage et al. |
| 8,735,844 B1 | 5/2014 | Khaykovich et al. |
| 8,737,565 B1 | 5/2014 | Lyon et al. |
| 8,744,048 B2 | 6/2014 | Lee et al. |
| 8,755,487 B2 | 6/2014 | Kaneko |
| 8,767,915 B2 | 7/2014 | Stutman |
| 8,767,916 B2 | 7/2014 | Hashimoto |
| 8,781,069 B2 | 7/2014 | Murakoshi |
| 8,824,629 B2 | 9/2014 | Ishii |
| 8,831,174 B2 | 9/2014 | Kohara |
| 8,831,175 B2 | 9/2014 | Silver et al. |
| 8,831,179 B2 | 9/2014 | Adler et al. |
| 8,855,265 B2 | 10/2014 | Engel |
| 8,861,682 B2 | 10/2014 | Okunuki et al. |
| 8,903,042 B2 | 12/2014 | Ishii |
| 8,908,824 B2 | 12/2014 | Kondoh |
| 8,995,622 B2 | 3/2015 | Adler et al. |
| 9,001,967 B2 | 4/2015 | Baturin |
| 9,008,278 B2 | 4/2015 | Lee et al. |
| 9,016,943 B2 | 4/2015 | Jacobsen et al. |
| 9,020,101 B2 | 4/2015 | Omote et al. |
| 9,063,055 B2 | 6/2015 | Ouchi |
| 9,129,715 B2 | 9/2015 | Adler et al. |
| 9,222,899 B2 | 12/2015 | Yamaguchi |
| 9,257,254 B2 | 2/2016 | Ogura et al. |
| 9,263,225 B2 | 2/2016 | Morton |
| 9,329,141 B2 | 5/2016 | Stutman |
| 9,357,975 B2 | 6/2016 | Baturin |
| 9,390,881 B2 | 7/2016 | Yun et al. |
| 9,439,613 B2 | 9/2016 | Stutman |
| 9,448,190 B2 | 9/2016 | Yun et al. |
| 9,449,781 B2 | 9/2016 | Yun et al. |
| 9,494,534 B2 | 11/2016 | Baturin |
| 9,543,109 B2 | 1/2017 | Yun et al. |
| 9,564,284 B2 | 2/2017 | Gerzoskovitz |
| 9,570,265 B1 | 2/2017 | Yun et al. |
| 9,594,036 B2 | 3/2017 | Yun et al. |
| 9,632,040 B2 | 4/2017 | Stutman |
| 9,719,947 B2 | 8/2017 | Yun et al. |
| 9,757,081 B2 | 9/2017 | Proksa |
| 9,761,021 B2 | 9/2017 | Koehler |
| 9,823,203 B2 | 11/2017 | Yun et al. |
| 9,826,949 B2 | 11/2017 | Ning |
| 9,837,178 B2 | 12/2017 | Nagai |
| 9,842,414 B2 | 12/2017 | Koehler |
| 9,861,330 B2 | 1/2018 | Rossl |
| 9,874,531 B2 | 1/2018 | Yun et al. |
| 9,881,710 B2 | 1/2018 | Roessl |
| 9,916,655 B2 | 3/2018 | Sampanoni |
| 9,939,392 B2 | 4/2018 | Wen |
| 9,970,119 B2 | 5/2018 | Yokoyama |
| 10,014,148 B2 | 7/2018 | Tang et al. |
| 10,028,716 B2 | 7/2018 | Rossl |
| 10,045,753 B2 | 8/2018 | Teshima |
| 10,068,740 B2 | 9/2018 | Gupta |
| 10,074,451 B2 | 9/2018 | Kottler et al. |
| 10,085,701 B2 | 10/2018 | Hoshino |
| 10,141,081 B2 | 11/2018 | Preusche |
| 10,151,713 B2 | 12/2018 | Wu et al. |
| 10,153,062 B2 | 12/2018 | Gall et al. |
| 10,182,194 B2 | 1/2019 | Karim et al. |
| 10,217,596 B2 | 2/2019 | Liang et al. |
| 10,247,683 B2 | 4/2019 | Yun et al. |
| 10,264,659 B1 | 4/2019 | Miller et al. |
| 10,176,297 B2 | 9/2019 | Zerhusen et al. |
| 2001/0006413 A1 | 7/2001 | Burghoorn |
| 2002/0085676 A1 | 7/2002 | Snyder |
| 2003/0142790 A1 | 1/2003 | Zhou et al. |
| 2003/0223536 A1 | 12/2003 | Yun et al. |
| 2004/0047446 A1 | 3/2004 | Platonov |
| 2004/0120463 A1 | 6/2004 | Wilson et al. |
| 2004/0140432 A1 | 7/2004 | Maldonado et al. |
| 2005/0074094 A1 | 4/2005 | Jen et al. |
| 2005/0123097 A1 | 6/2005 | Wang |
| 2005/0163284 A1 | 7/2005 | Inazuru |
| 2005/0282300 A1 | 12/2005 | Yun et al. |
| 2006/0045234 A1 | 3/2006 | Pelc |
| 2006/0062350 A1 | 3/2006 | Yokhin |
| 2007/0030959 A1 | 2/2007 | Ritter |
| 2007/0071174 A1 | 3/2007 | Hebert et al. |
| 2007/0108387 A1 | 5/2007 | Yun et al. |
| 2007/0110217 A1 | 5/2007 | Ukita |
| 2007/0183563 A1 | 8/2007 | Baumann |
| 2007/0183579 A1 | 8/2007 | Baumann et al. |
| 2007/0189449 A1 | 8/2007 | Baumann |
| 2007/0248215 A1 | 10/2007 | Ohshima et al. |
| 2008/0084966 A1 | 4/2008 | Aoki et al. |
| 2008/0089484 A1 | 4/2008 | Reinhold |
| 2008/0094694 A1 | 4/2008 | Yun et al. |
| 2008/0116398 A1 | 5/2008 | Hara |
| 2008/0159707 A1 | 7/2008 | Lee et al. |
| 2008/0165355 A1 | 7/2008 | Yasui et al. |
| 2008/0170662 A1 | 7/2008 | Reinhold |
| 2008/0170668 A1 | 7/2008 | Kruit et al. |

(56) References Cited

U.S. PATENT DOCUMENTS

| | | |
|---|---|---|
| 2008/0181363 A1 | 7/2008 | Fenter et al. |
| 2008/0240344 A1 | 10/2008 | Reinhold |
| 2008/0273662 A1 | 11/2008 | Yun |
| 2009/0052619 A1 | 2/2009 | Endoh |
| 2009/0092227 A1 | 4/2009 | David |
| 2009/0154640 A1 | 6/2009 | Baumann et al. |
| 2009/0316860 A1 | 12/2009 | Okunuki et al. |
| 2010/0012845 A1 | 1/2010 | Baeumer et al. |
| 2010/0027739 A1 | 2/2010 | Lantz et al. |
| 2010/0040202 A1 | 2/2010 | Lee |
| 2010/0046702 A1 | 2/2010 | Chen et al. |
| 2010/0061508 A1 | 3/2010 | Takahashi |
| 2010/0091947 A1 | 4/2010 | Niu |
| 2010/0141151 A1 | 6/2010 | Reinhold |
| 2010/0246765 A1 | 9/2010 | Murakoshi |
| 2010/0260315 A1 | 10/2010 | Sato et al. |
| 2010/0272239 A1 | 10/2010 | Lantz et al. |
| 2010/0284513 A1 | 11/2010 | Kawabe |
| 2011/0026680 A1 | 2/2011 | Sato |
| 2011/0038455 A1 | 2/2011 | Silver et al. |
| 2011/0058655 A1 | 3/2011 | Okumura et al. |
| 2011/0064191 A1 | 3/2011 | Toth et al. |
| 2011/0085644 A1 | 4/2011 | Verman |
| 2011/0135066 A1 | 6/2011 | Behling |
| 2011/0142204 A1 | 6/2011 | Zou et al. |
| 2011/0235781 A1 | 9/2011 | Aoki et al. |
| 2011/0243302 A1 | 10/2011 | Murakoshi |
| 2011/0268252 A1 | 11/2011 | Ozawa et al. |
| 2012/0041679 A1 | 2/2012 | Stampanoni |
| 2012/0057669 A1 | 3/2012 | Vogtmeier et al. |
| 2012/0163547 A1 | 6/2012 | Lee et al. |
| 2012/0163554 A1 | 6/2012 | Tada |
| 2012/0224670 A1 | 9/2012 | Kiyohara et al. |
| 2012/0228475 A1 | 9/2012 | Pang et al. |
| 2012/0269323 A1 | 10/2012 | Adler et al. |
| 2012/0269324 A1 | 10/2012 | Adler |
| 2012/0269325 A1 | 10/2012 | Adler et al. |
| 2012/0269326 A1 | 10/2012 | Adler et al. |
| 2012/0294420 A1 | 11/2012 | Nagai |
| 2013/0011040 A1 | 1/2013 | Kido et al. |
| 2013/0032727 A1 | 2/2013 | Kondoe |
| 2013/0039460 A1 | 2/2013 | Levy |
| 2013/0108012 A1 | 5/2013 | Sato |
| 2013/0108022 A1 | 5/2013 | Kugland et al. |
| 2013/0195246 A1 | 8/2013 | Tamura et al. |
| 2013/0223594 A1 | 8/2013 | Sprong et al. |
| 2013/0259207 A1 | 10/2013 | Omote et al. |
| 2013/0279651 A1 | 10/2013 | Yokoyama |
| 2013/0308112 A1 | 11/2013 | Clube et al. |
| 2013/0308754 A1 | 11/2013 | Yamazaki et al. |
| 2014/0023973 A1 | 1/2014 | Marconi et al. |
| 2014/0037052 A1 | 2/2014 | Adler |
| 2014/0064445 A1 | 3/2014 | Adler |
| 2014/0072104 A1 | 3/2014 | Jacobsen et al. |
| 2014/0079188 A1 | 3/2014 | Hesselink et al. |
| 2014/0105363 A1 | 4/2014 | Chen et al. |
| 2014/0146945 A1 | 5/2014 | Fredenberg et al. |
| 2014/0153692 A1 | 6/2014 | Larkin et al. |
| 2014/0177800 A1 | 6/2014 | Sato et al. |
| 2014/0185778 A1 | 7/2014 | Lee et al. |
| 2014/0205057 A1 | 7/2014 | Koehler et al. |
| 2014/0211919 A1 | 7/2014 | Ogura et al. |
| 2014/0226785 A1 | 8/2014 | Stutman et al. |
| 2014/0241493 A1 | 8/2014 | Yokoyama |
| 2014/0270060 A1 | 9/2014 | Date et al. |
| 2014/0369469 A1 | 12/2014 | Ogura et al. |
| 2015/0030126 A1 | 1/2015 | Radicke |
| 2015/0030127 A1 | 1/2015 | Aoki et al. |
| 2015/0043713 A1 | 2/2015 | Chen |
| 2015/0049860 A1 | 2/2015 | Das |
| 2015/0055743 A1 | 2/2015 | Vedantham et al. |
| 2015/0055745 A1 | 2/2015 | Holzner et al. |
| 2015/0092924 A1 | 4/2015 | Yun et al. |
| 2015/0110252 A1 | 4/2015 | Yun et al. |
| 2015/0117599 A1 | 4/2015 | Yun et al. |
| 2015/0194287 A1 | 7/2015 | Yun et al. |
| 2015/0243397 A1 | 8/2015 | Yun et al. |
| 2015/0247811 A1 | 9/2015 | Yun et al. |
| 2015/0260663 A1 | 9/2015 | Yun et al. |
| 2015/0357069 A1 | 12/2015 | Yun et al. |
| 2016/0064175 A1 | 3/2016 | Yun et al. |
| 2016/0066870 A1 | 3/2016 | Yun et al. |
| 2016/0106387 A1 | 4/2016 | Kahn |
| 2016/0178540 A1 | 6/2016 | Yun et al. |
| 2016/0268094 A1 | 9/2016 | Yun et al. |
| 2016/0320320 A1 | 11/2016 | Yun et al. |
| 2016/0351370 A1 | 12/2016 | Yun et al. |
| 2017/0047191 A1 | 2/2017 | Yun et al. |
| 2017/0052128 A1 | 2/2017 | Yun et al. |
| 2017/0162288 A1 | 6/2017 | Yun et al. |
| 2017/0162359 A1 | 6/2017 | Tang et al. |
| 2017/0227476 A1 | 8/2017 | Zhang et al. |
| 2017/0234811 A1 | 8/2017 | Zhang et al. |
| 2017/0261442 A1 | 9/2017 | Yun et al. |
| 2017/0336334 A1 | 11/2017 | Yun et al. |
| 2018/0144901 A1 | 5/2018 | Yun et al. |
| 2018/0261352 A1 | 9/2018 | Matsuyama et al. |
| 2018/0306734 A1 | 10/2018 | Morimoto et al. |
| 2018/0323032 A1 | 11/2018 | Strelec et al. |
| 2018/0344276 A1 | 12/2018 | DeFreitas et al. |
| 2018/0348151 A1 | 12/2018 | Kasper et al. |
| 2018/0356355 A1 | 12/2018 | Momose et al. |
| 2019/0017942 A1 | 1/2019 | Filevich |
| 2019/0017946 A1 | 1/2019 | Wack et al. |
| 2019/0018824 A1 | 1/2019 | Zarkadas |
| 2019/0019647 A1 | 1/2019 | Lee et al. |
| 2019/0027265 A1 | 1/2019 | Dey et al. |
| 2019/0043689 A1 | 2/2019 | Camus |
| 2019/0064084 A1 | 2/2019 | Ullom et al. |
| 2019/0086342 A1 | 3/2019 | Pois et al. |
| 2019/0088439 A1 | 3/2019 | Honda |
| 2019/0113466 A1 | 4/2019 | Karim et al. |
| 2019/0115184 A1 | 4/2019 | Zalubovsky |
| 2019/0131103 A1 | 5/2019 | Tuohimaa |
| 2019/0132936 A1 | 5/2019 | Steck et al. |

FOREIGN PATENT DOCUMENTS

| | | |
|---|---|---|
| EP | 0432568 | 6/1991 |
| EP | 0751533 | 1/1997 |
| EP | 1028451 | 8/2000 |
| FR | 2548447 | 1/1985 |
| JP | H06-188092 | 7/1994 |
| JP | H07-056000 | 3/1995 |
| JP | H08-184572 | 7/1996 |
| JP | 2000-306533 | 11/2000 |
| JP | 2003-288853 | 10/2003 |
| JP | 2004-089445 | 3/2004 |
| JP | 2007-218683 | 8/2007 |
| JP | 2007-265981 | 10/2007 |
| JP | 2007-311185 | 11/2007 |
| JP | 2008-200359 | 4/2008 |
| JP | 2008-145111 | 6/2008 |
| JP | 2008-197495 | 8/2008 |
| JP | 2009-195349 | 3/2009 |
| JP | 2009-212058 | 9/2009 |
| JP | 2010-236986 | 10/2010 |
| JP | 2011-029072 | 2/2011 |
| JP | 2011-218147 | 11/2011 |
| JP | 2012-032387 | 2/2012 |
| JP | 2012-187341 | 10/2012 |
| JP | 2012-254294 | 12/2012 |
| JP | 2013-508683 | 3/2013 |
| JP | 2013-157269 | 8/2013 |
| JP | 2013-160637 | 8/2013 |
| JP | 2013-239317 | 11/2013 |
| JP | 2015-002074 | 1/2015 |
| JP | 2015-047306 | 3/2015 |
| JP | 2015-077289 | 4/2015 |
| WO | WO 1995/006952 | 3/1995 |
| WO | WO 1998/011592 | 3/1998 |
| WO | WO 2002/039792 | 5/2002 |
| WO | WO 2003/081631 | 10/2003 |
| WO | WO 2005/109969 | 11/2005 |

(56) References Cited

FOREIGN PATENT DOCUMENTS

| | | |
|---|---|---|
| WO | WO 2006/096052 | 9/2006 |
| WO | WO 2007/1125833 | 11/2007 |
| WO | WO 2009/098027 | 8/2009 |
| WO | WO 2009/1104560 | 8/2009 |
| WO | WO 2011/032572 | 3/2011 |
| WO | WO 2012/032950 | 3/2012 |
| WO | WO 2013/004574 | 1/2013 |
| WO | WO 2013/111050 | 8/2013 |
| WO | WO 2013/118593 | 8/2013 |
| WO | WO 2013/160153 | 10/2013 |
| WO | WO 2013/168468 | 11/2013 |
| WO | WO 2014/054497 | 4/2014 |
| WO | WO 2015/016019 | 2/2015 |
| WO | WO 2015/034791 | 3/2015 |
| WO | WO 2015/066333 | 5/2015 |
| WO | WO 2015/084466 | 6/2015 |
| WO | WO 2015/168473 | 11/2015 |
| WO | WO 2015/176023 | 11/2015 |
| WO | WO 2015/187219 | 12/2015 |
| WO | WO 2016/187623 | 11/2016 |
| WO | WO 2017/031740 | 3/2017 |
| WO | WO 2017/204850 | 11/2017 |
| WO | WO 2017/213996 | 12/2017 |
| WO | WO 2018/175570 | 9/2018 |

OTHER PUBLICATIONS

"Element Six CVD Diamond Handbook" (Element Six, Luxembourg, 2015).
"High performance benchtop EDXRF spectrometer with Windows® software," published by: Rigaku Corp., Tokyo, Japan; 2017.
"Monochromatic Doubly Curved Crystal Optics," published by: X-Ray Optical Systems, Inc. (XOS), East Greenbush, NY; 2017.
"Optics and Detectors," Section 4 of XS-Ray Data Booklet, 3rd Ed., A.C. Thompson ed. (Lawrence Berkeley Nat'l Lab, Berkeley, CA, 2009).
"Properties of Solids," Ch. 12 of CRC Handbook of Chemistry and Physics, 90th ed., Devid R. Lide & W.M. "Mickey" Haynes, eds. (CRC Press, Boca Raton, FL, 2009), pp. 12-41-12-46; 12-203-12-212.
"Science and Technology of Future Light Sources", Arthur L. Robinson (LBNL) and Brad Plummer (SLAG), eds. Report Nos. ANL-08/39 / BNL-81895-2008 / LBNL-1090E-2009 / SLAC-R-917 (Lawrence Berkeley Nal'l Lab, Berkeley, CA, Dec. 2008).
"Toward Control of Matter: Energy Science Needs for a New Class of X-Ray Light Sources" (Lawrence Berkeley Nal'l Lab, Berkeley, CA, Sep. 2008).
X-ray-Optics.de Website, http://www.x-ray-optics.de/, accessed Feb. 13, 2016.
"X-ray Optics for BES Light Source Facilities," Report of the Basic Energy Sciences Workshop on X-ray Optics for BES Light Source Facilities, D. Mills & H. Padmore, Co-Chairs, (U.S. Dept. of Energy, Office of Science, Potomac, MD, Mar. 2013).
Abullian et al., "Quantitative determination of the lateral density and intermolecular correlation between proteins anchored on the membrane surfaces using grazing incidence small-angle X-ray scattering and grazing incidence X-ray fluorescence," Nov. 28, 2012, The Journal of Chemical Physics, vol. 137, pp. 204907-1 to 204907-8.
Adachi et al., "Development of the 17-inch Direct-Conversion Dynamic Flat-panel X-ray Detector (FPD)," Digital R/F (Shimadzu Corp., 2 pages (no date, published-2004 with product release).
Aharonovich et al., "Diamond Nanophotonics," Adv. Op. Mat'ls vol. 2, Issue 10 (2014).
Als-Nielsen et al., "Phase contrast imaging" Sect. 9.3 of Ch. 9 of "Elements of Modern X-ray Physics, Second Edition" , (John Wiley & Sons Ltd, Chichester, West Sussex, UK, 2011), pp. 318-329.
Als-Nielsen et al., "Photoelectric Absorption," Ch. 7 of "Elements of Modern X-ray Physics, Second Edition," (John Wiley & Sons Ltd, Chichester, West Sussex, UK, 2011).

Als-Nielsen et al., "Refraction and reflection from interfaces," Ch. 3 of "Elements of Modern X-ray Physics, Second Edition," (John Wiley & Sons Ltd., Chichester, West Sussex, UK, 2011), pp. 69-112.
Als-Nielsen et al., "X-rays and their interaction with matter", and "Sources", Ch. 1 & 2 of "Elements of Modern X-ray Physics, Second Edition" (John Wiley & Sons Ltd, Chichester, West Sussex, UK, 2011).
Altapova et al., "Phase contrast laminography based on Talbot interferometry," Opt. Express, vol. 20, No. 6, (2012) pp. 6496-6508.
Ando et al., "Smooth and high-rate reactive ion etching of diamond," Diamond and Related Materials, vol. 11, (2002) pp. 824-827.
Arfelli et al., "Mammography with Synchrotron Radiation: Phase-Detection Techniques," Radiology vol. 215, (2000), pp. 286-293.
Arndt et al., Focusing Mirrors for Use with Microfocus X-ray Tubes, 1998, Journal of Applied Crystallography, vol. 31, pp. 733-741.
Bachucki et al., "Laboratory-based double X-ray spectrometer for simultaneous X-ray emission and X-ray absorption studies," J. Anal. Atomic Spectr. DOI:10.1039/C9JA00159J (2019).
Balaic et al., "X-ray optics of tapered capillaries," Appl. Opt. vol. 34 (Nov. 1995) pp. 7263-7272.
Baltes et al., "Coherent and incoherent grating reconstruction," J. Opt. Soc. Am. A vol. 3(8), (1986), pp. 1268-1275.
Barbee Jr., "Multilayers for x-ray optics," Opt. Eng. vol. 25 (Aug. 1986) pp. 898-915.
Baron et al., "A compact optical design for Bragg reflections near backscattering," J. Synchrotron Rad., vol. 8 (2001), pp. 1127-1130.
Bech, "In-vivo dark-field and phase-contrast x-ray imaging," Scientific Reports 3, (2013), Article number: 03209.
Bech, "X-ray imaging with a grating interferometer," University of Copenhagan PhD. Thesis, (May 1, 2009).
Bergamin et al., "Measuring small lattice distortions in Si-crystals by phase-contrast x-ray topography," J. Phys. D: Appl. Phys. vol. 33 (Dec. 31, 2000) pp. 2678-2682.
Bernstorff, "Grazing Incidence Small Angle X-ray Scattering (GISAXS)," Presentation at Advanced School on Synchrotron and Free Electron Laser Sources and their Multidisciplinary Applications, Apr. 2008, Trieste, Italy.
Bilderback et al., "Single Capillaries," Ch. 29 of "Handbook of Optics vol. III, 2nd Ed." (McGraw Hill, New York, 2001).
Birkholz, "Chapter 4: Grazing Incidence Configurations," Thin Film Analysis by X-ray Scattering (Wiley-VCH Verlag GmbH & Co. KGaA, Weinheim, Germany, 2006).
Bjeoumikhov et al., "A modular system for XRF and XRD applications consisting of a microfocus X-ray source and different capillary optics," X-ray Spectrometry, vol. 33 (2004), pp. 312-316.
Bjeoumikhov et al., "Capillary Optics for X-Rays," Ch. 18 of "Modern Developments in X-Ray and Neutron Optics," A. Erko et al., eds. (Springer, Berlin, Germany, 2008), pp. 287-306.
Canberra Model S-5005 WinAxil X-Ray Analysis Software, published by: Canberra Eurisys Benelux N.V./S.A.,Zellik, Belgium; Jun. 2004.
Cerrina, "The Schwarzschild Objective," Ch. 27 of "Handbook of Optics vol. III, 2nd Ed." (McGraw Hill, New York, 2001).
Chen et al., "Advance in detection of low sulfur content by wavelength dispersive XRF," Proceedings of the Annual ISA Analysis Division Symposium (2002).
Chen et al., "Doubly curved crystal (DCC) X-ray optics and applications," Powder Diffraction, vol. 17(2) (2002), pp. 99-103.
Chen et al., "Guiding and focusing neutron beams using capillary optics," Nature vol. 357 (Jun. 4, 1992), pp. 391-393.
Chervenak et al., "Experimental thick-target bremsstrahlung spectra from electrons in the range 10 to 30 keV", Phys. Rev. A vol. 12 (1975), pp. 26-33.
Chon, "Measurement of Roundness for an X-Ray Mono-Capillary Optic by Using Computed Tomography," J. Korean Phys. Soc. vol. 74, No. 9, pp. 901-906 (May 2019).
Coan et al., "In vivo x-ray phase contrast analyzer-based imaging for longitudinal osteoarthritis studies in guinea pigs," Phys. Med. Biol. vol. 55(24) (2010), pp. 7649-7662.

(56) References Cited

OTHER PUBLICATIONS

Cockcroft et al., "Chapter 2: Experimental Setups," Powder Diffraction: Theory and Practice, R.E. Dinnebier and S.J.L. Billinge, eds (Royal Society of Chemistry Publishing, London, UK, 2008).
Cohen et al., "Tunable laboratory extended x-ray absorption fine structure system," Rev. Sci. Instr. vol. 51, No. 3, Mar. 1980, pp. 273-277.
Cong et al., "Fourier transform-based iterative method for differential phase-contrast computed tomography", Opt. Lett. vol. 37 (2012), pp. 1784-1786.
Cornaby et al., "Advances in X-ray Microfocusing with Monocapillary Optics at CHESS," CHESS News Magazine (2009), pp. 63-66.
Cornaby et al., "Design of Single-Bounce Monocapillary X-ray Optics," Advances in X-ray Analysis: Proceedings of the 55th Annual Conference on Applications of X-ray Analysis, vol. 50, (International Centre for Diffraction Data (ICDD), 2007), pp. 194-200.
Cornaby, "The Handbook of X-ray Single Bounce Monocapillary Optics, Including Optical Design and Synchrotron Applications" (PhD Dissertation, Cornell University, Ithaca, NY, May 2008).
David et al., "Fabrication of diffraction gratings for hard x-ray phase contrast imaging," Microelectron. Eng. vol. 84, (2007), pp. 1172-1177.
David et al., "Hard X-ray phase imaging and tomography using a grating interferometer," Spectrochimica Acta Part B vol. 62 (2007) pp. 626-630.
Davis et al., "Bridging the Micro-to-Macro Gap: A New Application for Micro X-Ray Fluorescence," Microsc Microanal., vol. 17(3) (Jun. 2011), pp. 410-417.
Diaz et al., "Monte Carlo Simulation of Scatter Field for Calculation of Contrast of Discs in Synthetic CDMAM Images," In: Digital Mammography, Proceedings 10th International Workshop IWDM 2010 (Springer Verlag, Berlin Heidelberg), (2010), pp. 628-635 (9 pages). Jun. 18, 2010.
Ding et al., "Reactive Ion Etching of CVD Diamond Films for MEMS Applications," Micromachining and Microfabrication, Proc. SPIE vol. 4230 (2000), pp. 224-230.
Dobrovinskaya et al., "Thermal Properties," Sect. 2.1.5 of "Sapphire: Material, Manufacturing,, Applications" (Springer Science + Business Media, New York, 2009).
Dong et al., "Improving Molecular Sensitivity in X-Ray Fluorescence Molecular Imaging (XFMI) of Iodine Distribution in Mouse-Sized Phantoms via Excitation Spectrum Optimization," IEEE Access, vol. 6, pp. 56966-56976 (2018).
Erko et al., "X-ray Optics," Ch. 3 of "Handbook of Practical X-Ray Fluorescence Analysis," B. Beckhoff et al., eds. (Springer, Berlin, Germany, 2006), pp. 85-198.
Falcone et al., "New directions in X-ray microscopy," Contemporary Physics, vol. 52, No. 4, (Jul.-Aug. 2010), pp. 293-318.
Fernández-Ruiz, "TXRF Spectrometry as a Powerful Tool for the Study of Metallic Traces in Biological Systems," Development in Analytical Chemistry, vol. 1 (2014), pp. 1-14.
Freund, "Mirrors for Synchrotron Beamlines," Ch. 26 of "Handbook of Optics vol. III, 2nd Ed." (McGraw Hill, New York, 2001).
Ge et al., "Investigation of the partially coherent effects in a 2D Talbot interferometer," Anal. Bioanal. Chem. vol. 401, (2011), pp. 865-870. Apr. 29, 2011 pub Jun. 14, 2011.
Gibson et al., "Polycapillary Optics: An Enabling Technology for New Applications," Advances in X-ray Analysis, vol. 45 (2002), pp. 286-297.
Gonzales et al., "Angular Distribution of Bremsstrahlung Produced by 10-Kev and 20 Kev Electrons Incident on a Thick Au Target", in Application of Accelerators in Research and Industry, AIP Conf. Proc. 1221 (2013), pp. 114-117.
Gonzales et al., "Angular distribution of thick-target bremsstrahlung produced by electrons with initial energies ranging from 10 to 20 keV incident on Ag", Phys. Rev. A vol. 84 (2011): 052726.
Guttmann et al., "Ellipsoidal capillary as condenser for the BESSSY full-field x-ray microscope," J. Phys. Conf. Ser. vol. 186 (2009): 012064.
Harasse et al., "Iterative reconstruction in x-ray computed laminography from differential phase measurements", Opt. Express. vol. 19 (2011), pp. 16560-16573.
Harasse et al., "X-ray Phase Laminography with a Grating Interferometer using Iterative Reconstruction", in International Workshop on X-ray and Neutron Phase Imaging with Gratings, AIP Conf. Proc. vol. 1466, (2012), pp. 163-168.
Harasse et al., "X-ray Phase Laminography with Talbot Interferometer", in Developments in X-Ray Tomography VII, Proc. SPIE vol. 7804 (2010), 780411.
Hasse et al., "New developments in laboratory-based x-ray sources and optics," Adv. in Laboratory-based X-Ray Sources, Optics, and Applications VI, ed. A.M. Khounsary, Proc. SPIE vol. 10387, 103870B-1 (2017).
Hemraj-Benny et al., "Near-Edge X-ray Absorption Fine Structure Spectroscopy as a Tool for Investigating Nanomaterials," Small, vol. 2(1), (2006), pp. 26-35.
Henke et al., "X-ray interactions: photoabsorption, scattering, transmission, and reflection at E=50–30000 eV, Z=1–92," Atomic Data and Nuclear Data Tables, vol. 54 (No. 2) (Jul. 1993), pp. 181-342.
Hennekam et al., "Trace metal analysis of sediment cores using a novel X-ray fluorescence core scanning method," Quaternary Int'l, https://doi.org/10.1016/j.quaint.2018.10.018 (2018).
Honma et al., Full-automatic XAFS Measurement System of the Engineering Science Research II beamline BL14B2 at Spring-8, 2011, AIP Conference Proceedings 1234, pp. 13-16.
Howard et al., "High-Definition X-ray Fluorescence Elemental Mapping of Paintings," Anal. Chem., 2012, vol. 84(7), pp. 3278-3286.
Howells, "Gratings and Monochromators in the VUV and Soft X-Ray Spectral Region," Ch. 21 of Handbook of Optics vol. III, 2nd Ed. (McGraw Hill, New York, 2001).
Howells, "Mirrors for Synchrotron-Radiation Beamlines," Publication LBL-34750 (Lawrence Berkeley Laboratory, Berkeley, CA, Sep. 1993).
Hrdý et al, "Diffractive-Refractive Optics: X-ray Crystal Monochromators with Profiled Diffracting Surfaces," Ch. 20 of "Modern Developments in X-Ray and Neutron Optics," A. Erko et al., eds. (Springer, Berlin Heidelberg New York, 2008).
Hwang et al, "New etching process for device fabrication using diamond," Diamond & Related Materials, vol. 13 (2004) pp. 2207-2210.
Ide-Ektessabi et al., "The role of trace metallic elements in neurodegenerative disorders: quantitative analysis using XRF and XANES spectroscopy," Anal. Sci., vol. 21(7) (Jul. 2005), pp. 885-892.
Ihsan et al., "A microfocus X-ray tube based on a microstructured X-ray target", Nuclear Instruments and Methods in Physics Research B vol. 267 (2009) pp. 3566-3573.
Ishisaka et al., "A New Method of Analyzing Edge Effect in Phase Contrast Imaging with Incoherent X-rays," Optical Review, vol. 7, No. 6, (2000), pp. 566-572.
Ito et al., "A Stable In-Laboratory EXAFS Measurement System," Jap. J. Appl. Phys., vol. 22, No. 2, Feb. 1, 1983, pp. 357-360.
Itoh et al., "Two-dimensional grating-based X-ray phase-contrast imaging using Fourier transform phase retrieval," Op. Express, vol. 19, No. 4 (2011) pp. 3339-3346.
Janssens et al, "Recent trends in quantitative aspects of microscopic X-ray fluorescence analysis," TrAC Trends in Analytical Chemistry 29.6 (Jun. 2010): 464-478.
Jahrman et al., "Vacuum formed temporary spherically and toroidally bent crystal analyzers for x-ray absorption and x-ray emission spectroscopy," Rev. Sci. Inst. vol. 90, 013106 (2019).
Jiang et al., "X-Ray Phase—Contrast Imaging with Three 2D Gratings," Int. J. Biomed. Imaging, (2008), 827152, 8 pages.
Joy, "Astronomical X-ray Optics," Ch. 28 of "Handbook of Optics vol. III, 2nd Ed.," (McGraw Hill, New York, 2001).
Kalasova et al., "Characterization of a laboratory-based X-ray computed nonotomography system for propagation-based method of phase contrast imaging," IEEE Trans. on Instr. and Meas., DOI 10.1109/TIM.2019.2910338 (2019).

(56) References Cited

OTHER PUBLICATIONS

Keyrilainen et al., "Phase contrast X-ray imaging of breast," Acta Radiologica, vol. 51 (8), (2010), pp. 866-884. Jan. 18, 2010 pub Jun. 15, 2010.
Kidalov et al., "Thermal Conductivity of Diamond Composites," Materials, vol. 2 (2009) pp. 2467-2495.
Kido et al., "Bone Cartilage Imaging with X-ray Interferometry using a Practical X-ray Tube", in Medical Imaging 2010: Physics of Medical Imaging, Proc. SPIE vol. 7622 (2010), 762240.
Kim, "Talbot images of wavelength-scale amplitude gratings," Opt. Express vol. 20(5), (2012), pp. 4904-4920.
Kim et al., "Observation of the Talbot Effect at Beamline 6C Bio Medical Imaging of he Pohang Light Source-II," J. Korean Phys. Soc., vol. 74, No. 10, pp. 935-940 (May 2019).
Kirkpatrick et al., "Formation of Optical Images by X-Rays", J. Opt. Soc. Am. vol. 38(9) (1948), pp. 766-774.
Kirz, "Phase zone plates for x rays and the extreme uv," J. Op. Soc. Am. vol. 64 (Mar. 1974), pp. 301-309.
Kirz et al., "The History and Future of X-ray Microscopy", J. Physics: Conden. Series vol. 186 (2009): 012001.
Kiyohara et al., "Development of the Talbot-Lau Interferometry System Available for Clinical Use", in International Workshop on X-ray and Neutron Phase Imaging with Gratings, AIP Cong. Proc. vol. 1466, (2012), pp. 97-102.
Klockenkämper et al., "7.1 Instrumental Developments" and "7.3 Future Prospects by Combinations," from Chapter 7 of Total Reflection X-ray Fluorescence Analysis and Related Methods 2nd Ed. (J. Wiley and Sons, Hoboken, NJ, 2015).
Klockenkämper et al., "Chapter 3: Instrumentation for TXRF and GI-XRF," Total Reflection X-ray Fluorescence Analysis and Related Methods 2nd Ed. (J. Wiley and Sons, Hoboken, NJ, 2015).
Kottler et al., "A two-directional approach for grating based differential phase contrast imaging using hard x-rays," Opt. Express vol. 15(3), (2007), pp. 1175-1181.
Kottler et al., "Dual energy phase contrast x-ray imaging with Talbot-Lau interferometer," J. Appl. Phys. vol. 108(11), (2010), 114906. Jul. 7, 2010 pub Dec. 7, 2010.
Kumakhov et al., "Multiple reflection from surface X-ray optics," Physics Reports, vol. 191(5), (1990), pp. 289-350.
Kumakhov, "X-ray Capillary Optics. History of Development and Present Status" in Kumakhov Optics and Application, Proc. SPIE 4155 (2000), pp. 2-12.
Kuwabara et al., "Hard-X-ray Phase-Difference Microscopy with a Low-Brilliance Laboratory X-ray Source", Appl. Phys. Express vol. 4 (2011) 062502.
Kuznetsov, "X-Ray Optics Calculator," Institute of Microelectronics Technology and High Purity Materials, Russian Academy of Sciences (IMT RAS), Chernogolovka, Russia (6 pages submitted); 2016.
Lagomarsino et al., "Reflective Optical Arrays," Ch. 19 of "Modern Developments in X-Ray and Neutron Optics," A. Erko et al. eds. (Springer, Berlin, Germany, 2008), pp. 307-317.
Lai, "X-Ray Microfocusing Optics," Slide Presentation from Argonne National Laboratory, 71 slides, Cheiron Summer School 2007.
Langhoff et al., "X-ray Sources," Ch. 2 of "Handbook of Practical X-Ray Fluorescence Analysis," B. Beckhoff et al., eds. (Springer, Berlin Heidelberg New York, 2006), pp. 33-82.
Lechner et al., "Silicon drift detecors for high count rate X-ray spectroscopy at room temperature," Nuclear Instruments and Methods, vol. 458A (2001), pp. 281-287.
Leenaers et al., "Application of Glancing Incidence X-ray Analysis," 1997, X-ray Spectrometry, vol. 26, pp. 115-121.
Lengeler et al., "Refractive X-ray Optics," Ch. 20 of "Handbook of Optics vol. III, 2nd Ed." (McGraw Hill, New York, 2001.
Li et al., "Source-optic-crystal optimisation for compact monochromatic imaging," Proc. SPIE 5537 (2004), pp. 105-114.
Li et al., "X-ray phase-contrast imaging using cascade Talbot-Lau interferometers," Proc. SPIE 10964 (2018), pp. 1096469-1-1096469-6.

Lohmann et al., "An interferometer based on the Talbot effect," Optics Communications vol. 2 (1971), pp. 413-415.
Lübcke et al., "Soft X-ray nanoscale imaging using a sub-pixel resolution charge coupled device (CCD) camera," Ref. Sci. Instrum. vol. 90, 043111 (2019).
Lühl et al., "Scanning transmission X-ray microscopy with efficient X-ray fluorescence detection (STXM-XRF) for biomedical applications in the soft and tender energy range," J. Synch. Rad. vol. 26, https://doi.org/10.1107/S1600577518016879, (2019).
MacDonald et al., "An Introduction to X-ray and Neutron Optics," Ch. 19 of "Handbook of Optics vol. III, 2nd Ed." (McGraw Hill, New York, 2001).
MacDonald et al., "Polycapillary and Multichannel Plate X-Ray Optics," Ch. 30 of "Handbook of Optics vol. III, 2nd Ed.," (McGraw Hill, New York, 2001).
MacDonald et al., "Polycapillary X-ray Optics for Microdiffraction," J. Appl. Cryst., vol. 32 (1999) pp. 160-167.
MacDonald, "Focusing Polycapillary Optics and Their Applications," X-Ray Optics and Instrumentation, vol. 2010, (Oct. 2010): 867049.
Maj et al., "Etching methods for improving surface imperfections of diamonds used for x-ray monochromators," Adv. X-ray Anal., vol. 48 (2005), pp. 176-182.
Malgrange, "X-ray Optics for Synchrotron Radiation," ACTA Physica Polinica A, vol. 82(1) (1992) pp. 13-32.
Malzer et al., "A laboratory spectrometer for high throughput X-ray emission spectroscopy in catalysis research," Rev. Sci. Inst. 89, 113111 (2018).
Masuda et al., "Fabrication of Through-Hole Diamond Membranes by Plasma Etching Using Anodic Porous Alumina Mask," Electrochemical and Solid-State Letters, vol. 4(11) (2001) pp. G101-G103.
Matsushita, "Mirrors and Multilayers," Slide Presentation from Photon Factor, Tsukuba, Japan, 65 slides, (Cheiron School 2009, Sprint-8, Japan, Nov. 2009).
Matsushita, "X-ray monochromators," Slide Presentation from Photon Factory, Tsukuba, Japan, 70 slides, (Cheiron School 2009, Spring-8, Japan, Nov. 2009).
Matsuyama et al., "Wavefront measurement for a hard-X-ray nanobeam using single-grating interferometry", Opt Express vol. 20 (2012), pp. 24977-24986.
Miao et al., "Motionless phase stepping in X-ray phase contrast imaging with a compact source," Proceedings of the National Academy of Sciences, vol. 110(48), (2013), pp. 19268-19272.
Michette, "Zone and Phase Plates, Bragg-Fresnel Optics," Ch. 23 of "Handbook of Optics vol. III, 2nd Ed.," (McGraw Hill, New York, 2001).
Mizutani et al., X-ray microscopy for neural circuit reconstruction in 9th International Conference on X-Ray Microscopy, J. Phys: Conf. Ser. 186 (2009) 012092.
Modregger et al., "Grating-Based X-ray Phase Contrast Imaging," Ch. 3 of Emerging Imaging Technologies in Medicine, M. Anastasio & P. La Riviere, ed., CRC Press, Boca Raton, FL, (2012), pp. 43-56.
Momose et al., "Biomedical Imaging by Talbot-Type X-Ray Phase Tomography" in Developments in X-Ray Tomography V, Proc. SPIE vol. 6318 (2006) 63180T.
Momose et al., "Grating-Based X-ray Phase Imaging Using Multiline X-ray Source", Jpn. J. Appl. Phys. vol. 48 (2009), 076512.
Momose et al., "Phase Tomography by X-ray Talbot Interferometry for Biological Imaging" Jpn. J. Appl. Phys. vol. 45 2006 pp. 5254-5262.
Momose et al., "Phase Tomography Using X-ray Talbot Interferometer", in Synchrotron Radiation Instrumentation: Ninth International Conference, AIP Conf. Proc. vol. 879 (2007), pp. 1365-1368.
Momose et al., "Phase-Contrast X-Ray Imaging Using an X-Ray Interferometer for Biological Imaging", Analytical Sciences vol. 17 Supplement (2001), pp. i527-i530.
Momose et al., "Sensitivity of X-ray Phase Imaging Based on Talbot Interferometry", Jpn. J. Appl. Phys. vol. 47 (2008), pp. 8077-8080.
Momose et al., "X-ray Phase Measurements with Talbot Interferometry and Its Applications", in International Conference on Advanced Phase Measurement Methods in Optics and Imaging, AIP Conf. Proc. vol. 1236 (2010), pp. 195-199.

(56) References Cited

OTHER PUBLICATIONS

Momose et al., "X-ray Phase Imaging—From Static Observation to Dynamic Observation—", in International Workshop on X-ray and Neutron Phase Imaging with Gratings AIP Conf. Proc. vol. 1466, (2012), pp. 67-77.
Momose et al., "X-ray Phase Imaging Using Lau Effect", Appl. Phys. Express vol. 4 (2011) 066603.
Momose et al., "X-Ray Phase Imaging with Talbot Interferometry", in "Biomedical Mathematics: Promising Directions in Imaging, Therapy Planning, and Inverse Problems", Y. Censor, M. Jiang & G.Wang, eds. (Medical Physics Publishing, Madison, WI, USA, 2010), pp. 281-320.
Momose et al., "X-ray phase tomography with a Talbot interferometer in combination with an X-ray imaging microscope", in 9th International Conference on X-Ray Microscopy, J. Phys: Conf. Ser. 186 (2009) 012044.
Momose et al., "X-ray Talbot Interferometry with Capillary Plates", Jpn. J. Appl. Phys. vol. 45 (2006), pp. 314-316.
Momose et al., "Four-dimensional X-ray phase tomography with Talbot interferometry and white synchrotron radiation: dynamic observation of a living worm", Opt. Express vol. 19 (2011), pp. 8423-8432.
Momose et al., "High-speed X-ray phase imaging and X-ray phase tomography with Talbot interferometer and white synchrotron radiation", Opt. Express vol. 17 (2009), pp. 12540-12545.
Momose et al., "Phase Imaging with an X-ray Talbot Interferometer", Advances in X-ray Analysis vol. 49(3) (2006), pp. 21-30.
Momose et al.,"Demonstration of X-Ray Talbot Interferometry", Jpn. J. Appl. Phys. vol. 42 (2003), pp. L866-L868.
Momose et al.,"Phase Tomography Using an X-ray Talbot Interferometer", in Developments in X-Ray Tomography IV, Proc. SPIE vol. 5535 (2004), pp. 352-360.
Momose, "Recent Advances in X-ray Phase Imaging", Jpn. J. Appl. Phys. vol. 44 (2005), pp. 6355-6367.
Montgomery, "Self Imaging Objects of Infinite Aperture," J. Opt. Soc. Am. vol. 57(6), (1967), pp. 772-778.
Morimoto et al., "Development of multiline embedded X-ray targets for X-ray phase contrast imaging," XTOP 2012 Book of Abstracts, (Ioffe Physical-Technical Institute of the Russian Academy of Sciences, St. Petersburg, Russia, 2012), pp. 74-75.
Morimoto et al., X-ray phase contrast imaging by compact Talbot-Lau interferometer with a signal transmission grating, 2014, Optics Letters, vol. 39, No. 15, pp. 4297-4300.
Munro et al., Design of a novel phase contrast imaging system for mammography, 2010, Physics in Medicine and Biology, vol. 55, No. 14, pp. 4169-4185.
Nango et al., "Talbot-defocus multiscan tomography using the synchrotron X-ray microscope to study the lacuno-canalicular network in mouse bone", Biomed. Opt. Express vol. 4 (2013), pp. 917-923.
Neuhausler et al., "Non-destructive high-resolution X-ray imaging of ULSI micro-electronics using keV X-ray microscopy in Zernike phase contrast," Microelectronic Engineering, Elsevier Publishers BV., Amsterdam, NO, vol. 83, No. 4-9 (Apr. 1, 2006) pp. 1043-1046.
Newville, "Fundamentals of XAFS," (Univ. of Chicago, Chicago, IL, Jul. 23, 2004).
Noda et al., "Fabrication of Diffraction Grating with High Aspect Ratio Using X-ray Lithography Technique for X-ray Phase Imaging," Jpn. J. Appl. Phys. vol. 46, (2007), pp. 849-851.
Noda et al., "Fabrication of High Aspect Ratio X-ray Grating Using X-ray Lithography" J. Solid Mech_ Mater. Eng. vol. 3 (2009) pp. 416-423.
Nojeh, "Carbon Nanotube Electron Sources: From Electron Beams to Energy Conversion and Optophononics", ISRN Nanomaterials vol. 2014 (2014): 879827.
Nuhn, "From storage rings to free electron lasers for hard x-rays", J.A37 Phys.: Condens. Matter vol. 16 (2004), pp. S3413-S34121.
Nykanen et al., "X-ray scattering in full-field digital mammography," Med. Phys. vol. 30(7), (2003), pp. 1864-1873.

Oji et al., Automatic XAFS measurement system developed at BL14B2 in SPring-8, Available online Nov. 15, 2011, Journal of Synchrotron Radiation, vol. 19, pp. 54-59.
Olbinado et al., "Demonstration of Stroboscopic X-ray Talbot Interferometry Using Polychromatic Synchrotron and Laboratory X-ray Sources", Appl. Phys. Express vol. 6 (2013), 096601.
Ortega et al., "Bio-metals imaging and speciation in cells using proton and synchrotron radiation X-ray microspectroscopy," J. Royal Society Interface vol. 6 suppl. 5 (Oct. 6, 2009), pp. 6S649-58.
Otendal et al., A 9 keV electron-impact liquid-gallium-jet x-ray source, Rev. Sci. Instrum. vol. 79 (2008): 016102.
Oxford Instruments Inc., Series 5000 Model XTF5011 X-ray Tube information, Jun. 1998, 3 pages.
Parrill et al., "GISAXS—Glancing Incidence Small Angle X-ray Scattering," Journal de Physique IV, vol. 3 (Dec. 1993), pp. 411-417.
PAXSCAN Flat Panel X-ray Imaging, Varian Sales Brochure, (Varian Medical Systems, Palo Alto, CA, Nov. 11, 2004).
Pfeiffer et al., " Hard-X-ray dark-field imaging using a grating interferometer," Nature Materials vol. 7, (2008), pp. 134-137.
Pfeiffer et al., "Hard x-ray phase tomography with low brilliance x-ray sources," Phys. Rev. Lett. vol. 98, (2007), 108105.
Pfeiffer et al., "Phase retrieval and differential phase-contrast imaging with low-brilliance X-ray sources," Nature Physics vol. 2, (2006), pp. 258-261.
Pfeiffer, "Milestones and basic principles of grating-based x-ray and neutron phase-contrast imaging," in International Workshop on X-ray and Neutron Phase Imaging with Gratings AIP Conf. Proc. vol. 1466, (2012), pp. 2-11.
Pianetta et al., "Application of synchrotron radiation to TXRF analysis of metal contamination on silicon wafer surfaces," Thin Solid Films, vol. 373(1-2), 2000, pp. 222-226.
Potts, "Electron Probe Microanalysis", Ch. 10 of "A Handbook of Silicate Rock Analysis" (Springer Science + Business Media, New York, 1987), pp. 326-382 (equation quoted from p. 336).
Prewitt et al., "FIB Repair of 5X Recticles and Effects on IC Quality," Integrated Circuit Metrology, Inspection, and Process Control VII, Proc. SPIE vol. 1926 (1993), pp. 517-526.
Prewitt et al., "Focused ion beam repair: staining of photomasks and reticles," J. Phys. D Appl. Phys. vol. 26 (1993), pp. 1135-1137.
Prewitt et al., "Gallium Staining in FIB Repair of Photomasks," Microelectronic Engineering, vol. 21 (1993), pp. 191-196.
Qin et al., "Trace metal imaging with high spatial resolution: Applications in biomedicine," Metallomics, vol. 3 (Jan. 2011), pp. 28-37.
Rayleigh, "On copying diffraction gratings and some phenomena connected therewith," Philos. Mag. vol. 11 (1881), pp. 196-205.
Renaud et al., "Probing surface and interface morphology with Grazing Incidence Small Angle X-ray Scattering," Surface Science Reports, vol. 64:8 (2009), pp. 255-380.
Riege, "Electron Emission from Ferroelectrics—A Review", CERN Report CERN AT/93-18 (CERN, Geneva, Switzerland, Jul. 1993).
Röntgen, "Ueber eine neue Art von Strahlen (Wurzburg Verlag, Warzburg, Germany, 1896) also, in English, On a New Kind of Rays," Nature vol. 53 (Jan. 23, 1896). pp. 274-276.
Rovezzi, "Study of the local order around magnetic impurities in semiconductors for spintronics." PhD Dissertation, Condensed Matter, Universite Joseph-Fourier—Grenoble I, 2009, English <tel-00442852>.
Rutishauser, "X-ray grating interferometry for imaging and metrology," 2003, Eth Zurich, Diss. ETH No. 20939.
Sato et al., Two-dimensional gratings-based phase-contrast imaging using a conventional x-ray tube, 2011, Optics Letters, vol. 36, No. 18, pp. 3551-3553.
Scherer et al., "Bi-Directional X-Ray Phase-Contrast Mammography," PLoS One, vol. 9, Issue 5 (May 2014) e93502.
Scholz, "X-ray Tubes and Monochromators," Technical Workshop EPIV, Universität Würzburg (2007); 41 slides, 2007.
Scholze et al., "X-ray Detectors and XRF Detection Channels," Ch. 4 of "Handbook of Practical X-Ray Fluorescence Analysis," B. Beckhoff et al., eds. (Springer, Berlin Heidelberg, Germay, 2006), pp. 85-198.

(56) References Cited

OTHER PUBLICATIONS

Scordo et al., "Pyrolitic Graphite Mosaic Drystal Thickness and Mosaicity Optimization for an Extended Source Von Hamos X-ray Spectrometer," Condens. Matter Vo. 4, pp. 38-52 (2019).

Scott, "Hybrid Semiconductor Detectors for High Spatial Resolution Phase-contrast X-ray Imaging," Thesis, University of Waterloo, Department of Electrical and Computer Engineering, 2019.

Sebert, "Flat-panel detectors:how much better are they?" Pediatr. Radiol. vol. 36 (Suppl 2), (2006), pp. 173-181.

Seifert et al., "Talbot-Lau x-ray phase-contrast setup for fast scanning of large samples," Sci. Rep. 9:4199, pp. 1-11 (2019).

Shen, "Polarizing Crystal Optics," Ch. 25 of "Handbook of Optics vol. III, 2nd Ed.," (McGraw Hill, New York, 2001).

Shields et al., "Overview of Polycapillary X-ray Optics," Powder Diffraction, vol. 17(2) (Jun. 2002), pp. 70-80.

Shimura et al., "Hard x-ray phase contrast imaging using a tabletop Talbot-Lau interferometer with multiline embedded x-ray targets", Opt. Lett. vol. 38(2) (2013), pp. 157-159.

Siddons, "Crystal Monochromators and Bent Crystals," Ch. 22 of "Handbook of Optics vol. III, 2nd Ed.," (McGraw Hill, New York, 2001).

Smith, "Fundamentals of Digital Mammography:Physics, Technology and Practical Considerations," Publication R-BI-016 (Hologic, Inc., Bedford, MA, Mar. 2005).

Snigirev et al., "Hard X-Ray Microoptics," Ch. 17 of "Modern Developments in X-Ray and Neutron Optics," A. Erko et al., eds (Springer, Berlin, Germany, 2008), pp. 255-285.

Sparks Jr., "X-ray Fluorescence Microprobe for Chemical Analysis," in Synchrotron Radiation Research, H. Winick & S. Doniach, eds. (Plenum Press, New York, NY 1980), pp. 459-512.

Spiller, "Multilayers," Ch. 24 of "Handbook of Optics vol. III, 2nd Ed.," (McGraw Hill, New York, 2001).

Stampanoni et al., "The First Analysis and Clinical Evaluation of Native Breast Tissue Using Differential Phase-Contrast Mammography," Investigative Radiology, vol. 46, pp. 801-806. pub 2011-12-xx.

Struder et al., "Silicon Drift Detectors for X-ray Imaging," Presentation at Detector Workshop on Synchrotron Radiation Instrumentation, 54 slides, (Argonne Nat'l Lab, Argonne, IL Dec. 8, 2005), available at: <http://www.aps.anl.gov/News/Conferences/2005/Synchrotron_Radiation_Instrumentation/Presentations/Strueder.pdf>.

Strüder et al., "X-Ray Detectors," Ch. 4 of "X-ray Spectrometry: Recent Technological Advances," K. Tsuji et al. eds. (John Wiley & Sons, Ltd. Chichester, West Sussex, UK, 2004), pp. 63-131.

Stupple et al., "Modeling of Heat Transfer in an Aluminum X-Ray Anode Employing a Chemical Vapor Deposited Diamond Heat Spreader," J. Heat Transfer, Vo. 140, 124501-1-5 (Dec. 2018).

Sun et al., "Combined optic system based on polycapillary X-ray optics and single-bounce monocapillary optics for focusing X-rays from a conventional laboratory X-ray source," Nucl. Inst. and Methods in Phys. Res. A 802 (2015) pp. 5-9.

Sun et al., "Numerical design of in-line X-ray phase-contrast imaging based on ellipsoidal single-bounce monocapillary," Nucl. Inst. and Methods in Phys. Res. A746 (2014) pp. 33-38.

Sunday et al., "X-ray Metrology for the Semiconductor Industry Tutorial," J. Res. Nat'l Inst. Stan. vol. 124: 124003 (2019); https://doi.org/10.6028/jres.124.003.

Suzuki et al., "Hard X-ray Imaging Microscopy using X-ray Guide Tube as Beam Condenser for Field Illumination," J. Phys.: Conf. Ser. vol. 463 (2013): 012028.

Suzuki, "Development of the DIGITEX Safire Cardiac System Equipped with Direct conversion Flat Panel Detector," Digital Angio Technical Report (Shimadzu Corp., Kyoto, Japan, no date, published—2004 with product release).

Takahama, "RADspeed safire Digital General Radiography System Equipped with New Direct-Conversion FPD," Medical Now, No. 62 (2007).

Takeda et al., "Differential Phase X-ray Imaging Microscopy with X-ray Talbot Interferometer" Appl. Phys. Express vol. 1 (2008) 117002.

Takeda et al., "X-Ray Phase Imaging with Single Phase Grating", Jpn. J. Appl. Phys. vol. 46 (2007), pp. L89-L91.

Takeda et al., "In vivo physiological saline-infused hepatic vessel imaging using a two-crystal-interferometer-based phase-contrast X-ray technique", J. Synchrotron Radiation vol. 19 (2012), pp. 252-256.

Talbot, "Facts relating to optical science No. IV," Philos. Mag. vol. 9 (1836), pp. 401-407.

Tanaka et al., "Cadaveric and in vivo human joint imaging based on differential phase contrast by X-ray Talbot-Lau interferometry", Z. Med. Phys. vol. 23 (2013), pp. 222-227.

Tang et al., "Micro-computed tomography (Micro-CT): a novel appraoch for intraoperative breast cancer specimen imaging," Breast Cancer Res. Treat. vol. 139, pp. 311-316 (2013).

Taniguchi et al., "Diamond nanoimprint lithography," Nanotechnology, vol. 13 (2002) pp. 592-596.

Terzano et al., Recent advances in analysis of trace elements in environmental samples by X-ray based techniques (IUPAC Technical Report), Pure Appl. Chem. 2019.

Tkachuk et al., "High-resolution x-ray tomography using laboratory sources", in Developments in X-Ray Tomography V, Proc. SPIE 6318 (2006): 631810.

Tkachuk et al., "Multi-length scale x-ray tomography using laboratory and synchrotron sources", Microsc. Microanal. vol. 13 (Suppl. 2) (2007), pp. 1570-1571.

Töpperwien et al., "Multiscale x-ray phase-contrast tomography in a mouse model of transient focal cerebral ischemia," Biomed. Op. Express, vol. 10, No. 1, Jan. 2019, pp. 92-103.

Touzelbaev et al., "Applications of micron-scale passive diamond layers for the integrated circuits and microelectromechanical systems industries," Diamond and Rel. Mat'ls, vol. 7 (1998) pp. 1-14.

Tsuji et al., "X-Ray Spectrometry: Recent Technological Acvances," John Wiley & Sons Ltd. Chichester, West Susses, UK 2004), Chapters 1-7.

Udagawa, "An Introduction to In-House EXAFS Facilities," The Rigaku Journal, vol. 6, (1) (1989), pp. 20-27.

Udagawa, "An Introduction to X-ray Absorption Fine Structure," The Rigaku Journal, vol. 11(2)(1994), pp. 30-39.

Uehara et al., "Effectiveness of X-ray grating interferometry for non-destructive inspection of packaged devices", J. Appl. Phys. vol. 114 (2013), 134901.

Viermetz et al., "High resolution laboratory grating-based X-ray phase-contrast CT," Scientific Reports 8:15884 (2018).

Vogt, "X-ray Fluorescence Microscopy: A Tool for Biology, Life Science and Nanomedicine," Presentation on May 16, 2012 at James Madison Univ., Harrisonburg, VA (31 slides), 2012.

Wan et al.,"Fabrication of Multiple Slit Using Stacked-Sliced Method for Hard X-ray Talbot-Lau Interferometer", Jpn. J. Appl. Phys. vol. 47 (2008), pp. 7412-7414.

Wang et al., "Advantages of intermediate X-ray energies in Zernicke phase constrast X-ray microscopy," Biotech. Adv., vol. 31 (2013) pp. 387-392.

Wang et al., "Non-invasive classification of microcalcifications with phase-contrast X-ray mammography," Nature Comm. vol. 5:3797, pp. 1-9 (2014).

Wang, On the single-photon-counting (SPC) modes of imaging using an XFEL source, presented at IWORLD2015.

Wang et al., "Precise patterning of diamond films for MEMS application" Journal of Materials Processing Technology vol. 127 (2002), pp. 230-233.

Wansleben et al., "Photon flux determination of a liquid-metal jet x-ray source by means of photon scattering," arXiv:1903.06024v1, Mar. 14, 2019.

Weitkamp et al., "Design aspects of X-ray grating interferometry," in International Workshop on X-ray and Neutron Phase Imaging with Gratings AIP Conf. Proc. vol. 1466, (2012), pp. 84-89.

Weitkamp et al., "Hard X-ray phase imaging and tomography with a grating interferometer," Proc. SPIE vol. 5535, (2004), pp. 137-142.

(56) References Cited

OTHER PUBLICATIONS

Weitkamp et al., "X-ray wavefront diagnostics with Talbot interferometers," International Workshop on X-Ray Diagnostics and Scientific Application of the European XFEL, Ryn, Poland, (2010), 36 slides.
Weitkamp et al., Tomography with grating interferometers at low-brilliance sources, 2006, SPIE, vol. 6318, pp. 0S-1 to 0S-10.
Weitkamp et al., "X-ray phase imaging with a grating interferometer," Opt. Express vol. 13(16), (2005), pp. 6296-6304.
Weitkamp et al., "X-ray wavefront analysis and optics characterization with a grating interferometer," Appl. Phys. Lett. vol. 86, (2005), 054101.
Wen et al., "Fourier X-ray Scattering Radiography Yields Bone Structural Information," Radiology, vol. 251 (2009) pp. 910-918.
Wen et al., "Single-shot x-ray differential phase-contrast and diffraction imaging using two-dimensional transmission gratings," Op. Lett. vol. 35, No. 12, (2010) pp. 1932-1934.
Wittry et al., "Properties of fixed-position Bragg diffractors for parallel detection of x-ray spectra," Rev. Sci. Instr. vol. 64, pp. 2195-2200 (1993).
Wobrauschek et al., "Energy Dispersive, X-Ray Fluorescence Analysis," Encyclopedia of Analytical Chemistry, R.A. Meyers, Ed. (Wiley 2010).
Wobrauschek et al., "Micro XRF of light elements using a polycapillary lens and an ultra-thin window Silicon Drift Detector inside a vacuum chamber," 2005, International Centre for Diffraction Data 2005, Advances in X-ray Analysis, vol. 48, pp. 229-235.
Wolter, "Spiegelsysteme streifenden Einfalls als abbildende Optiken fur Rontgenstrahlen" [Grazing Incidence Reflector Systems as Imaging Optics for X-rays] Annalen der Physik vol. 445, Issue 1-2 (1952), pp. 94-114.
Yakimchuk et al., "Ellipsoidal Concentrators for Laboratory X-ray Sources: Analytical approaches for optimization," Mar. 22, 2013, Crystallography Reports, vol. 58, No. 2, pp. 355-364.
Yamamoto, "Fundamental physics of vacuum electron sources", Reports on Progress in Physics vol. 69, (2006), pp. 181-232.
Yanagihara et al., "X-Ray Optics," Ch. 3 of "X-ray Spectrometry: Recent Technological Advances," K. Tsuji et al. eds. (John Wiley & Sons, Ltd. Chichester, West Sussex, UK, 2004), pp. 63-131.
Yang et al., "Analysis of Intrinsic Stress in Diamond Films by X-ray Diffraction," Advances in X-ray Analysis, vol. 43 (2000), pp. 151-156.
Yashiro et al., "Distribution of unresolvable anisotropic microstructures revealed in visibility-contrast images using x-ray Talbot interferometry", Phys. Rev. B vol. 84 (2011), 094106.
Yashiro et al., "Hard x-ray phase-imaging microscopy using the self-imaging phenomenon of a transmission grating", Phys. Rev. A vol. 82 (2010), 043822.
Yashiro et al., "Theoretical Aspect of X-ray Phase Microscopy with Transmission Gratings" in International Workshop on X-ray and Neutron Phase Imaging with Gratings, AIP Conf. Proc. vol. 1466, (2012), pp. 144-149.
Yashiro et al., "X-ray Phase Imaging and Tomography Using a Fresnel Zone Plate and a Transmission Grating", in "The 10th International Conference on X-ray Microscopy Radiation Instrumentation", AIP Conf. Proc. vol. 1365 (2011) pp. 317-320.
Yashiro et al., "Efficiency of capturing a phase image using cone-beam x-ray Talbot interferometry", J. Opt. Soc. Am. A vol. 25 (2008), pp. 2025-2039.
Yashiro et al., "On the origin of visibility contrast in x-ray Talbot interferometry", Opt. Express (2010), pp. 16890-16901.
Yashiro et al., "Optimal Design of Transmission Grating for X-ray Talbot Interferometer", Advances in X-ray Analysis vol. 49(3) (2006), pp. 375-379.
Yashiro et al., "X-ray Phase Imaging Microscopy using a Fresnel Zone Plate and a Transmission Grating", in the 10th International Conference on Synchrotron Radiation Instrumentation, AIP Conf. Proc. vol. 1234 (2010), pp. 473-476.
Yashiro et. al., "Hard-X-Ray Phase-Difference Microscopy Using a Fresnel Zone Plate and a Transmission Grating", Phys. Rev. Lett. vol. 103 (2009), 180801.
Yu et al., "Morphology and Microstructure of Tungsten Films by Magnetron Sputtering," Mat. Sci. Forum, vol. 913, pp. 416-423 (2018).
Zanette et al., "Two-Dimensional X-Ray Grating interferometer," Phys. Rev. Lett. vol. 105 (2010) pp. 248102-1 248102-4.
Zeng et al., "Ellipsoidal and parabolic glass capillaries as condensers for x-ray microscopes," Appl. Opt. vol. 47 (May 2008), pp. 2376-2381.
Zeng et al., "Glass Monocapillary X-ray Optics and Their Applications in X-Ray Microscopy," X-ray Optics and Microanalysis: Proceedings of the 20th International Congress, AIP Conf. Proc. vol. 1221, (2010), pp. 41-47.
Zhang et al., "Application of confocal X-ray fluorescence based on capillary X-ray optics in nondestructively measuring the inner diameter of monocapillary optics," Optics Comm. (2018) https://doi.org/10.1016/j.optcom.2018.11.064.
Zhang et al., "Fabrication of Diamond Microstructures by Using Dry and Wet Etching Methods", Plasma Science and Technology vol. 15(6) (Jun. 2013), pp. 552-554.
Zhang et al., "Measurement of the inner diameter of monocapillary with confocal X-ray scattering technology based on capillary X-ray optics," Appl. Opt. (Jan. 8, 2019), doc ID 351489, pp. 1-10.

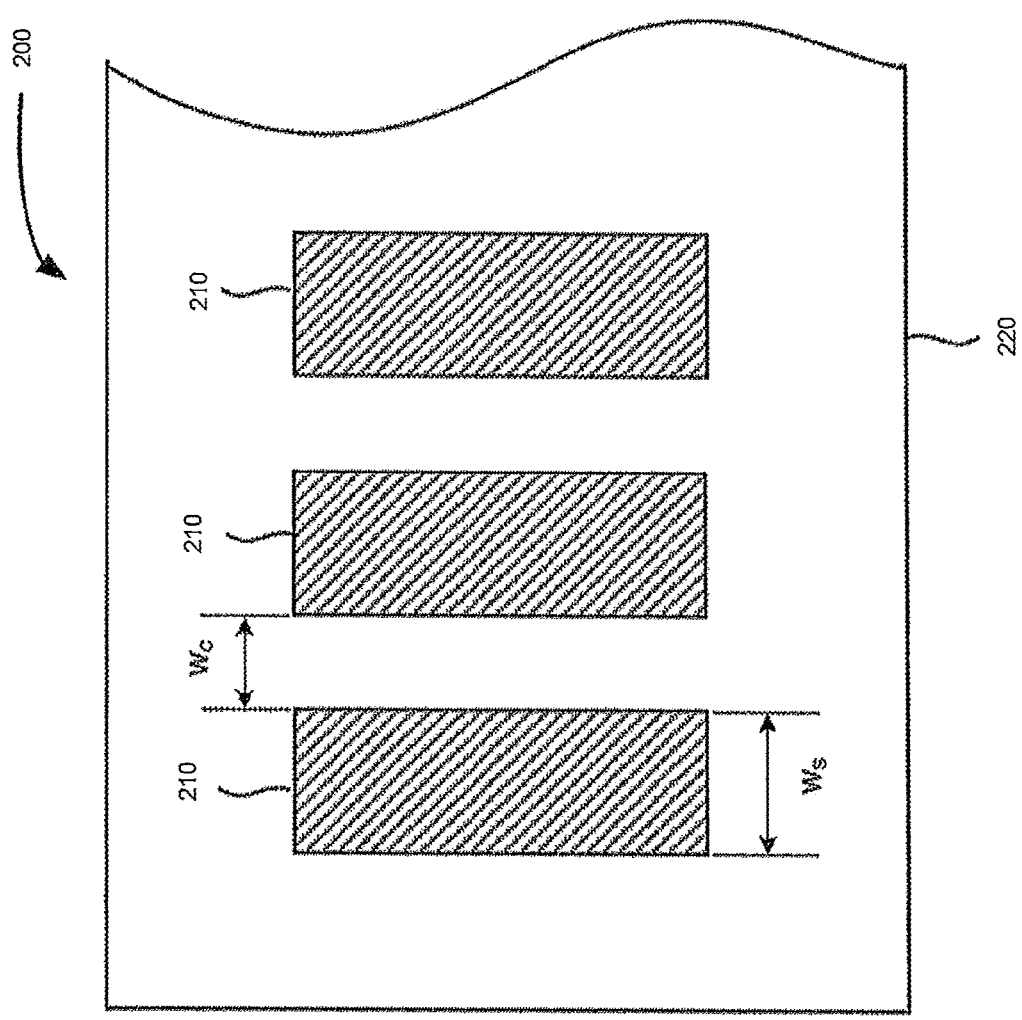

X-RAY EMISSION SPECTROMETER SYSTEM

CLAIM OF PRIORITY

This application claims the benefit of U.S. Provisional Appl. No. 62/651,883, filed Apr. 3, 2018 and incorporated in its entirety by reference herein.

BACKGROUND

Field

This application relates generally to x-ray spectroscopy systems, and more particularly, to x-ray emission spectroscopy (XES) systems.

Description of the Related Art

X-ray emission spectroscopy (XES) is a chemical speciation technique commonly employed at high brightness synchrotron light sources, but its application has been limited in laboratory systems due to the low brightness of laboratory x-ray sources and low spectral resolution of such systems which limit throughput. In attempts to overcome this deficiency, several academic groups have explored building x-ray emission spectroscopy systems using curved mosaic crystal analyzers in a von Hamos geometry for parallel detection of multiple x-ray energies.

SUMMARY

In certain embodiments, a system for x-ray emission spectroscopy is provided. The system comprises a mount configured to hold a sample, at least one x-ray source, and at least one x-ray optical train configured to focus x-rays from the at least one x-ray source to a focal spot and to irradiate a first side of the sample with the focused x-rays. The system further comprises at least one x-ray analyzer curved in at least one plane, the at least one x-ray analyzer configured to receive fluorescence x-rays emitted from the first side of the sample. The system further comprises at least one spatially-resolving x-ray detector, wherein the focal spot, the at least one x-ray analyzer, and the at least one spatially-resolving x-ray detector are positioned in an off-Rowland circle geometry.

In certain embodiments, an x-ray spectrometer is provided. The spectrometer comprises at least one x-ray optical train configured to receive fluorescence x-rays emitted from a sample impinged by electrons within an electron microscope and to focus at least some of the received fluorescence x-rays to a focal spot. The spectrometer further comprises at least one spatially-resolving x-ray detector and at least one x-ray analyzer curved in at least one plane. The at least one x-ray analyzer is configured to receive and diffract at least some of the focused fluorescence x-rays with x-rays of different wavelengths diffracted to different locations on the at least one spatially-resolving x-ray detector. The at least one x-ray analyzer and the at least one spatially-resolving x-ray detector are positioned on a Rowland circle.

In certain embodiments, a method for x-ray emission spectroscopy is provided. The method comprises irradiating a first side of a sample with a focused x-ray beam having a focal spot. The method further comprises receiving fluorescence x-rays emitted from the first side of the sample. The method further comprises diffracting, using at least one x-ray analyzer, at least some of the received fluorescence x-rays. Fluorescence x-rays with different wavelengths are diffracted towards different portions of at least one spatially-resolving x-ray detector, wherein the focal spot, the at least one x-ray analyzer, and the at least one spatially-resolving x-ray detector are positioned in an off-Rowland circle geometry.

In certain embodiments, a method for x-ray emission spectroscopy is provided. The method comprises receiving fluorescence x-rays emitted from a sample impinged by electrons within an electron microscope. The method further comprises focusing at least some of the received fluorescence x-rays to a focal spot. The method further comprises diffracting, using at least one x-ray analyzer, at least some of the focused fluorescence x-rays. Fluorescence x-rays with different wavelengths are diffracted towards different portions of at least one spatially-resolving x-ray detector. The at least one x-ray analyzer and the at least one spatially-resolving x-ray detector are positioned on a Rowland circle.

BRIEF DESCRIPTION OF THE DRAWINGS

FIGS. 3B and 3C schematically illustrate a top view and a perspective view, respectively, of a target comprising a plurality of example structures (e.g., microstructures) comprising different x-ray generating materials on a surface of the substrate in accordance with certain embodiments described herein.

DETAILED DESCRIPTION

Figure 1A:
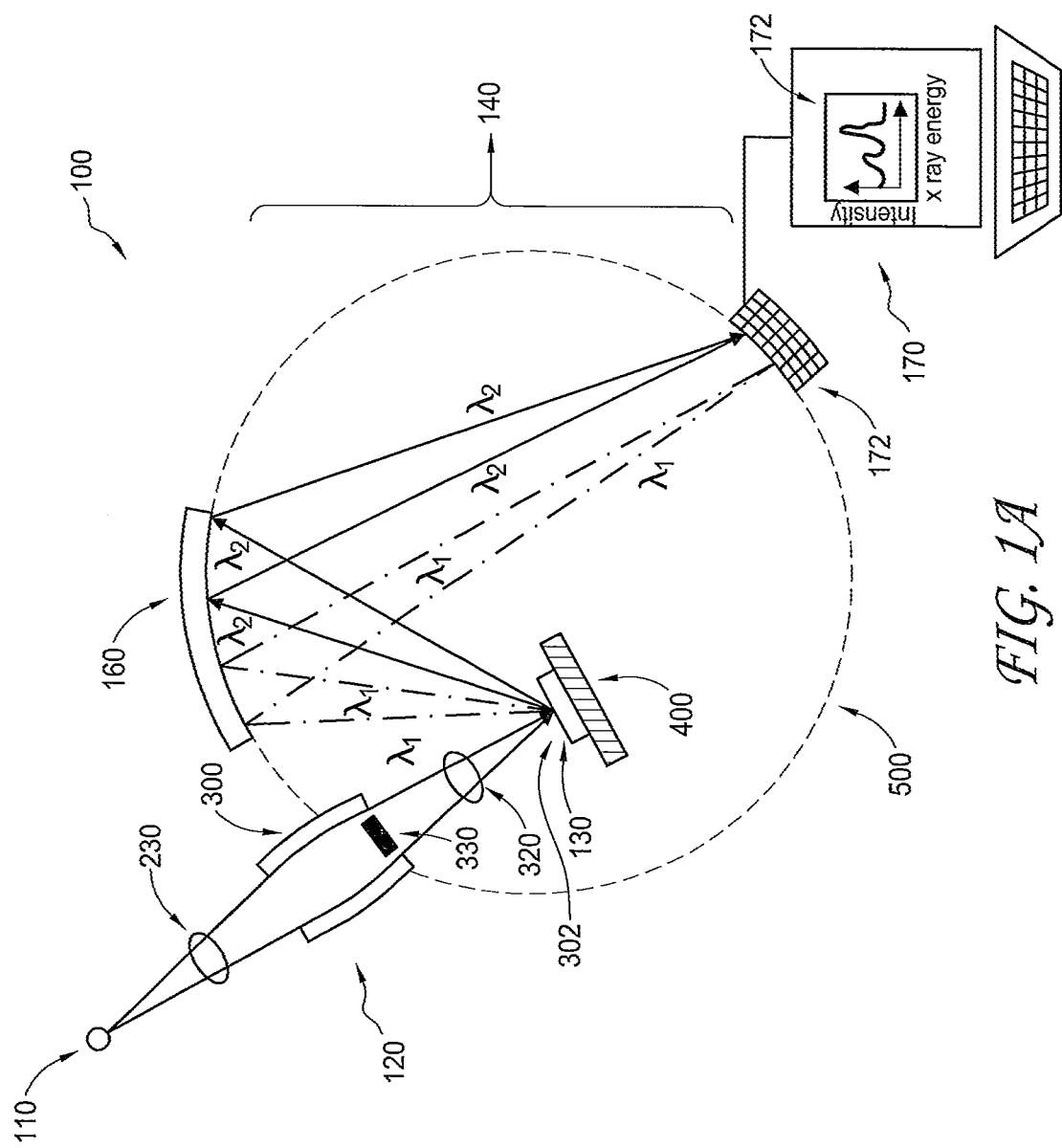
FIGS. 1A and 1B schematically illustrate example x-ray emission spectrometry (XES) systems in an "off-Rowland circle" geometry in accordance with certain embodiments described herein.

Certain embodiments described provide an x-ray spectroscopy system (e.g., an x-ray emission spectroscopy (XES) system) that employs at least one focusing x-ray optic, at least one x-ray analyzer, and at least one x-ray detector. In certain such embodiments, the focusing x-ray optic has an energy bandwidth greater than 10 eV and is configured to collect x-rays (e.g., from an x-ray source; from a sample emitting x-rays) and to focus at least a portion of the collected x-rays to a focal spot (e.g., on or in a sample; on an x-ray detector), the focal spot having a size (e.g., width; diameter) of less than or equal to 500 microns (e.g., less than or equal to 200 microns; less than or equal to 100 microns; less than or equal to 50 microns). The focal spot can serve as a source of diverging x-rays. In certain embodiments, the at least one x-ray optic comprises a capillary x-ray optic having an interior reflecting surface with a shape of a portion of a quadric surface and with a focal spot having a width (e.g., diameter) less than 15 microns. In certain embodiments, the focal spot serves as a source of x-rays of a Rowland circle single crystal or mosaic crystal spectrometer. Various embodiments described herein utilize a variety of x-ray materials and optical elements to provide a variety of x-ray bandwidth ranges suitable for a variety of x-ray spectroscopy applications.

Certain embodiments described herein provide an x-ray spectroscopy system that utilizes curved single crystal or mosaic crystal x-ray analyzers for parallel detection in conjunction with focusing x-ray optics, which provide secondary source points that enable substantially higher efficiency and which enable operation of laboratory x-ray sources at higher accelerating voltages for improved x-ray brightness. Certain embodiments advantageously provide a spectrometer system configured to perform XES measurements at high throughput and/or high spectral resolution. For example, the x-ray spectrometer system can be advantageously configured to provide fast XES measurements of high concentrations of one or more atomic elements within the sample (e.g., less than 10 minutes; less than 5 minutes; less than 2 minutes) and/or to provide highly sensitive XES measurements of low concentrations of one or more atomic elements within the sample (e.g., less than 5%, less than 2%, less than 1%).

In certain embodiments, the x-ray spectrometer system 100 is configured to perform x-ray emission spectroscopy (XES) and/or x-ray fluorescence spectroscopy (XFS) from a variety of samples (e.g., thin films with nanometer-scale thicknesses). For example, the x-ray spectrometer system 100 can be optimized for analysis of the Kβ lines (e.g., $K\beta_1$, $K\beta_2$, $K\beta_3$, $K\beta_5$) of transition metal elements or for analysis of Lβ lines of various elements. Certain such embodiments can be applied to a number of applications, including but not limited to: thin film analysis, in situ characterization of materials, or in operando measurements of batteries and other devices. In certain embodiments, the x-ray spectrometer system 100 is configured for use in high volume manufacturing environments or for semiconductor inspection.

In certain embodiments, the x-ray spectrometry (XES) system is an attachment to an electron microscope (e.g., encased in a vacuum housing). In certain such embodiments, the focal spot of the at least one x-ray optic enables operation of the XES system at large Bragg angles θ (e.g., greater than 60 degrees). In certain embodiments, the XES system is relatively compact (e.g., less than 12 cm in length) and is configured to achieve high peak resolution. In contrast to conventional electron microscope attachments (e.g., in which the x-ray source irradiates the sample within the electron microscope), certain embodiments described herein are advantageously able to achieve large Bragg angles θ for better spectral resolution. Such large Bragg angles θ are generally unavailable with conventional systems due to the practical space restrictions for wavelength dispersive spectrometers for electron microscopes (e.g., less than 16 cm).

Certain embodiments described herein provide an x-ray emission spectrometer (XES) that comprises an x-ray source, an x-ray optical train, and a Rowland circle geometry single crystal or mosaic crystal spectrometer. The x-ray source is configured to produce x-rays that are collected by the x-ray optical train which is configured to focus the x-rays onto an object to be examined (e.g., the sample) such that the focal spot (e.g., having a width of less than 15 microns) on the sample produces fluorescence x-rays. The focal spot is placed within a Rowland circle such that the sample's fluorescence x-rays are collected and dispersed by a curved single crystal or mosaic crystal toward a spatially-resolving x-ray detector to collect a bandwidth of x-ray energies simultaneously (e.g., parallel detection). In certain embodiments, a mount is configured to position the crystal spectrometer components relative to each other to enable incremental increases in the x-ray bandwidths which provide XES information.

In certain embodiments, a sample mount is configured to move the sample from within the Rowland circle toward the boundary of the Rowland circle as the x-ray energies are incremented, thereby enabling higher spectral resolution and greater efficiency for single x-ray energies (e.g., for determining weak emission lines such as valence-to-core (VtC) characteristic lines). In certain embodiments, the sample is translated in the plane perpendicular with respect to the x-ray beam for 2-D "mapping" by collecting the x-ray transmission spectrum. In certain embodiments, the sample is rotated about an axis, with or without translation, for 3D tomography by collecting the x-ray transmission spectrum.

Figure 1B:
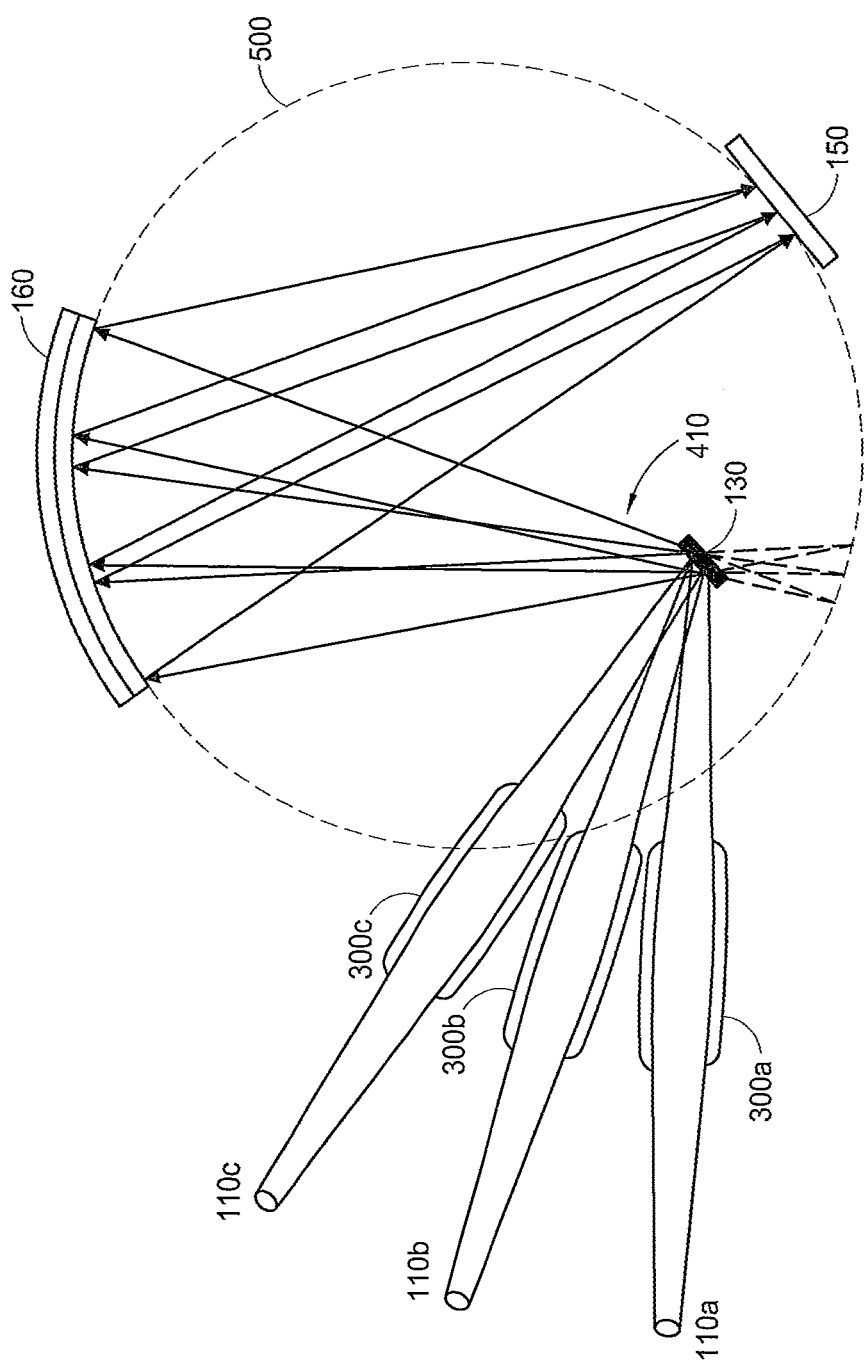

FIGS. 1A and 1B schematically illustrate example x-ray spectrometer systems 100 in accordance with certain embodiments described herein. In each of FIGS. 1A and 1B, the system 100 comprises at least one x-ray source 110, an x-ray optical system 120 that includes a sample 130 (e.g., an object to be examined), and an x-ray spectrometer 140 comprising at least one x-ray detector 150 and at least one x-ray analyzer 160. In certain embodiments, the system 100 further comprises an analysis system 170 (e.g., comprising signal processing electronics and a display 172) configured to correlate the intensity signals from the at least one x-ray detector 150 to the corresponding x-ray energies (see, e.g., FIG. 1A). As schematically illustrated by FIGS. 1A and 1B, the x-ray spectrometer system 100 has a "reflection" configuration (e.g., excitation x-rays or electrons impinging a side of the sample 130 and analyzing fluorescence x-rays emitted from the same side of the sample 130), in contrast to "transmission" configurations in which x-rays transmitted through the sample 130 are analyzed.

X-Ray Source

As schematically illustrated by FIG. 1A, in certain embodiments, the at least one x-ray source 110 comprises a single x-ray source 110. As schematically illustrated by FIG. 1B, in certain embodiments, the at least one x-ray source 110 comprises multiple x-ray sources 110a, 110b, 110c. In certain embodiments, the at least one x-ray source 110 comprises at least one x-ray source selected from the group consisting of: microfocus source (e.g., using electron bombardment of a solid anode target or a metal layer target deposited on a substrate), rotating anode source, and liquid metal anode type source (e.g., using liquid gallium metal jet as the anode).

In certain other embodiments, the at least one x-ray source 110 comprises at least one target 200 comprising a plurality of x-ray generating structures 210 (e.g., microstructures; stripes sputtered onto a substrate 220; wires brazed onto a substrate 220) comprising different x-ray generating materials in close thermal contact with at least one thermally conductive target substrate 220 (e.g., having a thermal conductivity greater than 100 W/mC at room temperature; diamond; copper). Various example x-ray sources 80 comprising at least one target 200 comprising a plurality of structures 210 compatible with certain embodiments described herein have been described in U.S. Pat. Nos. 9,390,881, 9,543,109, and U.S. Pat. Appl. Publ. Nos. 2016/0351370 and 2019/0011379, each of which is hereby incorporated herein by reference in its entirety. In addition, the at least one x-ray source 110 of certain embodiments can include various features (e.g., active cooling systems comprising channels that carry liquid near or into the at least one target microstructure 210 to remove heat).

Figure 2:
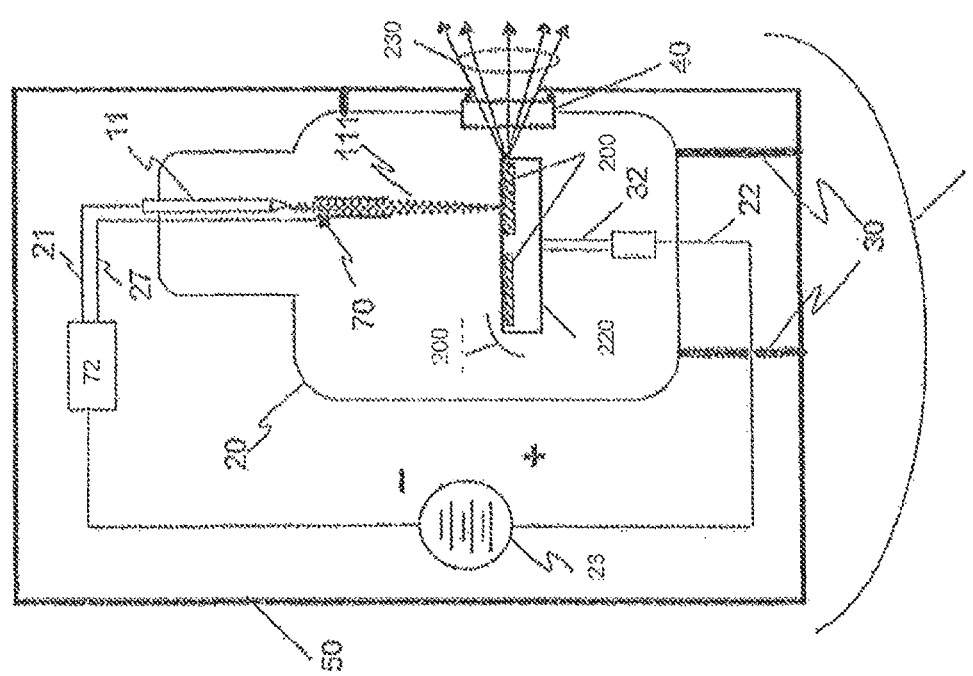
FIG. 2 schematically illustrates an example x-ray source in accordance with certain embodiments described herein.

FIG. 2 schematically illustrates an example x-ray source 110 in accordance with certain embodiments described herein. In certain embodiments, the at least one x-ray source 110 comprises a vacuum environment (e.g., $10^{-6}$ torr or better) maintained by a sealed vacuum chamber 20 or active pumping, and having sealed electrical leads 21, 22 that pass from the negative and positive terminals of a high voltage source 23 outside the vacuum chamber 20 to the various elements inside the vacuum chamber 20. The at least one x-ray source 110 of certain embodiments comprises one or more mounts 30 that secure the vacuum chamber 20 in a housing 50 (e.g., additionally comprising shielding material, such as lead, to prevent x-rays from being radiated from the at least one source 110 in unwanted directions). The at least one x-ray source 110 of certain embodiments further comprises at least one electron emitter 11 (e.g., cathode; metal electrode; nanostructures; carbon nanotubes; ferroelectric materials) inside the vacuum chamber 20, the at least one electron emitter 11 connected by the electrical lead 21 to the negative terminal of the high voltage source 23. The at least one electron emitter 11 is configured to generate at least one electron beam 111. Various techniques for electron beam generation are compatible with certain embodiments described herein, including but not limited to: thermionic emission, field emission, Schottky emission.

In certain embodiments, the at least one x-ray source 110 further comprises at least one target 200 comprising at least one target substrate 220 and one or more x-ray generating structures 210 comprising one or more x-ray generating materials in close thermal contact with the at least one target substrate 220. The at least one target substrate 220 is mounted to at least one target support 32 and is electrically connected by the opposite high voltage electrical lead 22 to be at ground or at a positive voltage relative to the at least one electron emitter 11, thus serving as an anode. The electrons of the electron beam 111 accelerate towards the at least one target 200 and collide with the at least one target 200 at high energy, with the energy of the electrons determined by the magnitude of the accelerating voltage (e.g., the voltage difference between the cathode and the anode). The collision of the electrons 111 into the at least one target 200 induces several effects, including the radiation of x-rays 230, some of which exit the vacuum chamber 20 and are transmitted through a window 40 transmissive to x-rays. In certain embodiments, the dimensions of the x-ray generating material and/or the focused electron beam 111 are such that the effective x-ray source spot size (e.g., width; diameter) is less than or equal to 50 microns. In certain embodiments, the window 40 is configured to allow at least some of the generated x-rays to be emitted from the x-ray source 110. For example, the window 40 (e.g., sheet or layer of aluminum) can be configured to filter the emitted x-rays by attenuating lower-energy x-rays while not appreciably affecting higher-energy x-rays.

In certain embodiments, the at least one x-ray source 110 further comprises an electron control system 70 (e.g., an electrostatic lens system or other system of electron optics in operative communication to a controller 72 by an additional electrical lead 27). The electron control system 70 is configured to control aspects of the electron beam 111 (e.g., direction; focus; spot size; electron flux; accelerating voltage) such that the electron beam 111 can be scanned, focused, de-focused, or otherwise directed onto the at least one target 200 (e.g., selected portions of the at least one target 200 comprising the one or more x-ray generating structures 210).

Figure 3A:
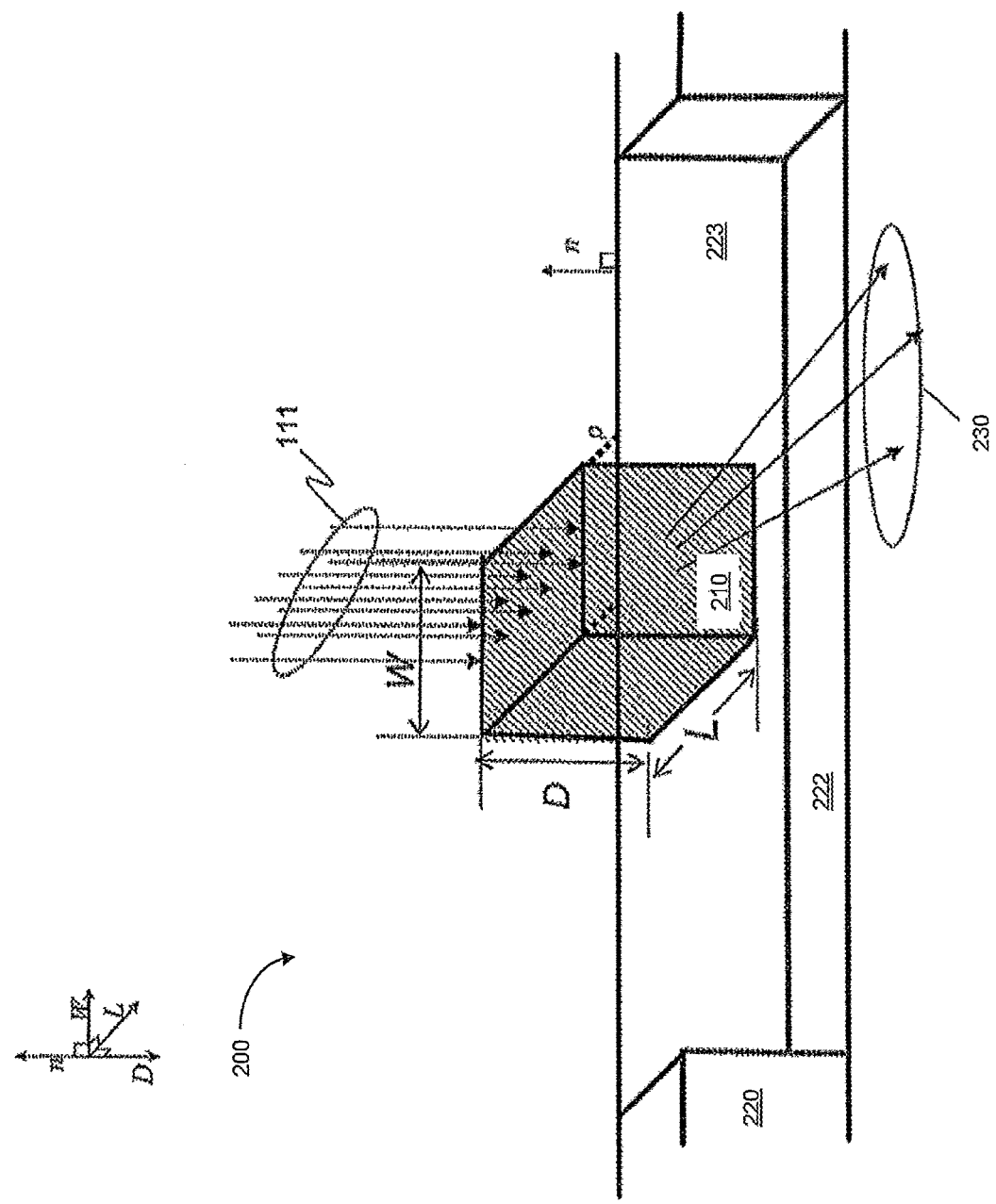
FIG. 3A schematically illustrates a portion of an example target comprising at least one structure on or in a substrate in accordance with certain embodiments described herein.

FIG. 3A schematically illustrates a portion of an example target 200 comprising at least one structure 210 on or in a substrate 220 in accordance with certain embodiments described herein. In certain embodiments, the at least one structure 210 comprises at least one microstructure. As used herein, the term "microstructure" refers to x-ray generating structures with at least one dimension smaller than 1 mm (e.g., greater than 10 nm). For example, at least one microstructure can have one dimension (e.g., length L) that is several millimeters or larger (e.g., in excess of 1 cm), with the other dimensions (e.g., width W and thickness D) that is less than or equal to 250 microns. The at least one microstructure of certain embodiments has a shape of a rectangular bar of width W, length L, and depth or thickness D that is configured to generate x-rays 230 when bombarded with electrons 111. In certain embodiments, the structure 210 of FIG. 3A is embedded into the substrate 220 at or near a recessed edge 223 of a recessed shelf 222 near an edge of the substrate 220. For example, the thickness D (e.g., along the surface normal of the substrate 220) can be between one-third and two-thirds of the electron penetration depth of the x-ray generating material of the structure 210 at the incident electron energy. The x-ray generating material used in the structure 210 of certain embodiments has good thermal properties and good x-ray production properties (e.g., x-ray production efficiency that is proportional to the material's atomic number; production of a predetermined specific x-ray spectrum of interest).

Figure 3C:
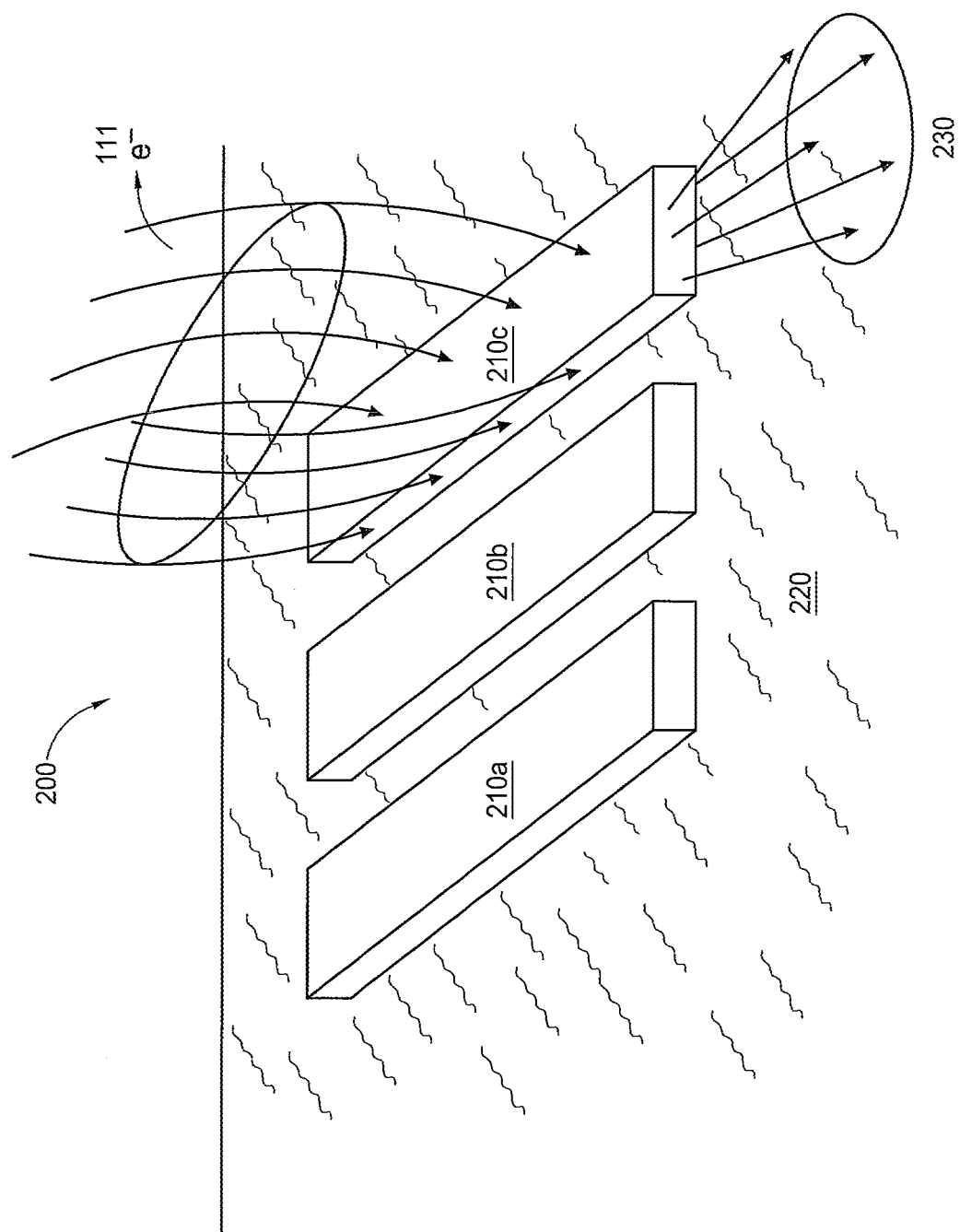
Figure 3D:
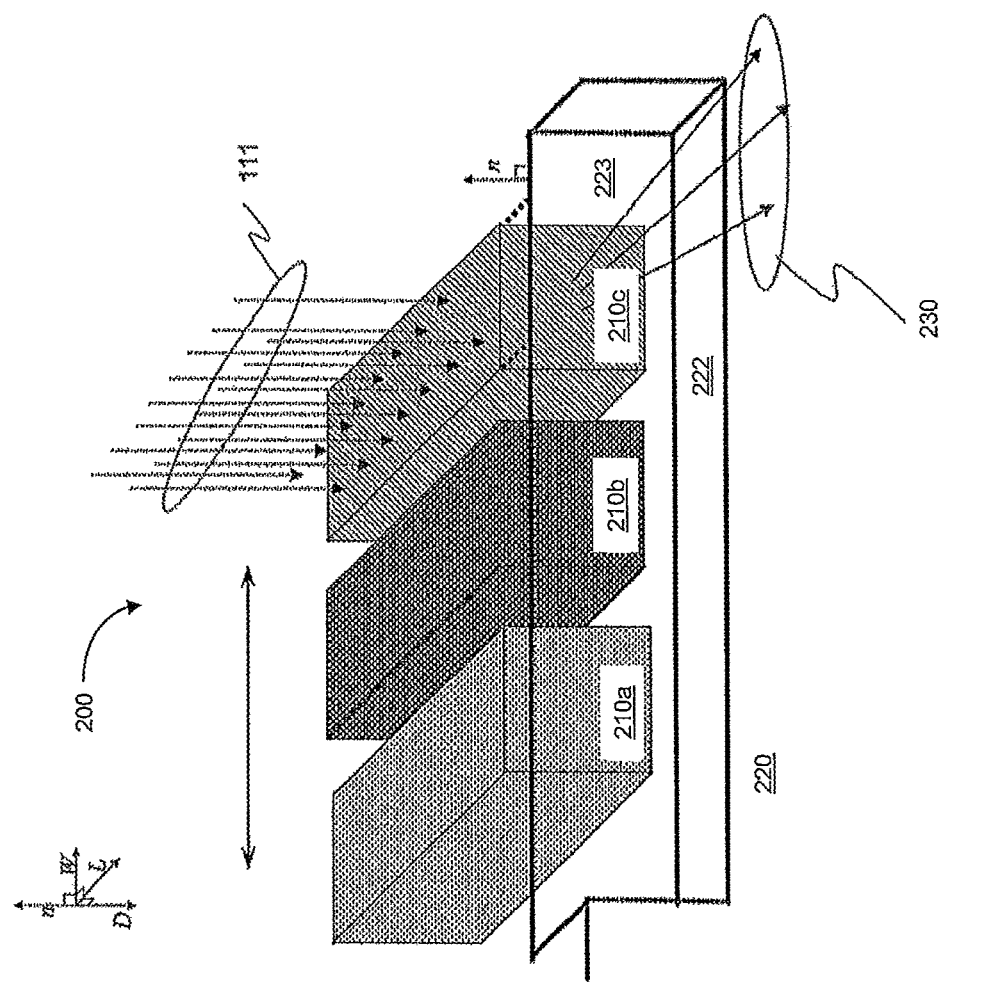
FIG. 3D schematically illustrates a perspective view of a target comprising a plurality of example structures (e.g., microstructures) comprising different x-ray generating materials embedded within the substrate in accordance with certain embodiments described herein.

FIGS. 3B and 3C schematically illustrate a top view and a perspective view, respectively, of a target 200 comprising a plurality of example structures 210a, 210b, 210c (e.g., microstructures) comprising different x-ray generating materials on a surface of the substrate 220 in accordance with certain embodiments described herein. FIG. 3D schematically illustrates a perspective view of a target 200 comprising a plurality of example structures 210a, 210b, 210c (e.g., microstructures) comprising different x-ray generating materials embedded within the substrate 220 in accordance with certain embodiments described herein. While FIG. 3D shows the structures 210a, 210b, 210c having ends that are positioned at or near a recessed edge 223 of a recessed shelf 222 near an edge of the substrate 220, in certain other embodiments, the structures 210 are completely encapsulated in the substrate 220.

In certain embodiments, one or more of the x-ray generating materials of the target 200 are selected from the group consisting of: Ti, Al, Cu, Cr, Fe, Mo, Rh, Co, W, Pt, Ag, and Au, and alloys that include one or more of these elements. In certain embodiments, two or more of the structures 210 comprises different x-ray generating materials from one another, allowing each structure 210 to generate x-rays with different spectra. For example, two or more of the structures 210 can comprise x-ray generating materials with different characteristic lines (e.g., Rh with a characteristic L$\alpha$ line of 2.7 keV; Ti with a characteristic K$\alpha$ line of 4.51 keV; Cr with a characteristic K$\alpha$ line of 5.4 keV; Mo; W; Au). In certain other embodiments, two or more of the structures 210 comprise the same x-ray generating material (e.g., to provide a longer use or lifetime of the system). In certain embodiments, the at least one structure 210 is in close thermal contact with the thermally conductive substrate 220 (e.g., by sputtering multiple materials upon the substrate 220 or by brazing multiple wire structures onto the surface of the substrate 220). In certain embodiments, the at least one structure 210 further comprises one or more layers 240 between the x-ray generating material and the substrate 220. For example, these layers 240 can comprise a diffusion-inhibiting material (e.g. Ta), a material configured to improve adhesion of the structure 210 to the substrate 220, and/or a material configured to improve the thermal conductance between the structure 210 and the substrate 220 (e.g. Cr between Cu and diamond). In certain embodiments, the at least one structure 210 further comprise one or more layers on top of the x-ray generating material. For example, these layers can comprise a thermally conducting overcoat and/or an electrically conducting overcoat.

In certain embodiments, the electron beam 111 propagates in a direction normal to the surface of the substrate 220 (see, e.g., FIGS. 3C and 3D), while in certain other embodiments, the electron beam 111 propagates along a direction that is non-normal to the surface of the substrate 220 (e.g., less than 40 degrees relative to the surface). One or both of the electron beam 111 and the at least one target 200 of certain embodiments are configured to be moved relative to each other (e.g., through mechanical movement of the electron source and/or the target 200; through electromagnetic mechanisms such as electron optics) such that at least one selected structure 210 of the target 200 is bombarded by the electron beam 111 and produces a corresponding x-ray spectra. In certain embodiments, the at least one x-ray generating material of the bombarded at least one structure 210 is selected to optimize the generation of x-rays at energies slightly above the absorption edge of a predetermined element of interest in the sample 130. As schematically illustrated by FIGS. 3C and 3D, the electron beam 111 can be focused onto one of the structures 210 to produce x-rays 230 at least some of which propagate in a set of cone angles (e.g., less than 3 degrees) centered around a take-off angle $\theta$ relative to the local surface (e.g., less than 30 degrees; between 0 and 6 degrees; between 0 and 15 degrees) and focused in an ellipse with a high aspect ratio.

As schematically illustrated by FIG. 3B, the structures 210 (e.g., wires; microstructures) can be spaced from one another by a distance we (e.g., 15 microns or more) and can each have a width w, (e.g., less than or equal to 300 microns; 250 microns). In certain embodiments, the distance we between the structures 210 can be selected to avoid creation of x-rays from an adjacent structure 210 when the electron beam 111 bombards a single target structure 210. The substrate 220 can extend past one or more ends of one or more of the structures 210 or the substrate 220 can be flush with one or more ends of one or more of the structures 210. In certain embodiments, as schematically illustrated by FIGS. 3A and 3D, the structures 210 are embedded within the substrate 220 and have a cross section in a plane perpendicular to the surface of the substrate 220 that is rectangular, curved, circular, square, or any other shape. In certain embodiments, as schematically illustrated by FIGS. 3B-3D, one or more of the structures 210 can have an aspect ratio (e.g., ratio of the length L along the surface of the substrate 220 to the width W along the surface of the substrate 220) that is greater than 3, greater than 5, greater than 10, or greater than 20.

Figure 3E:
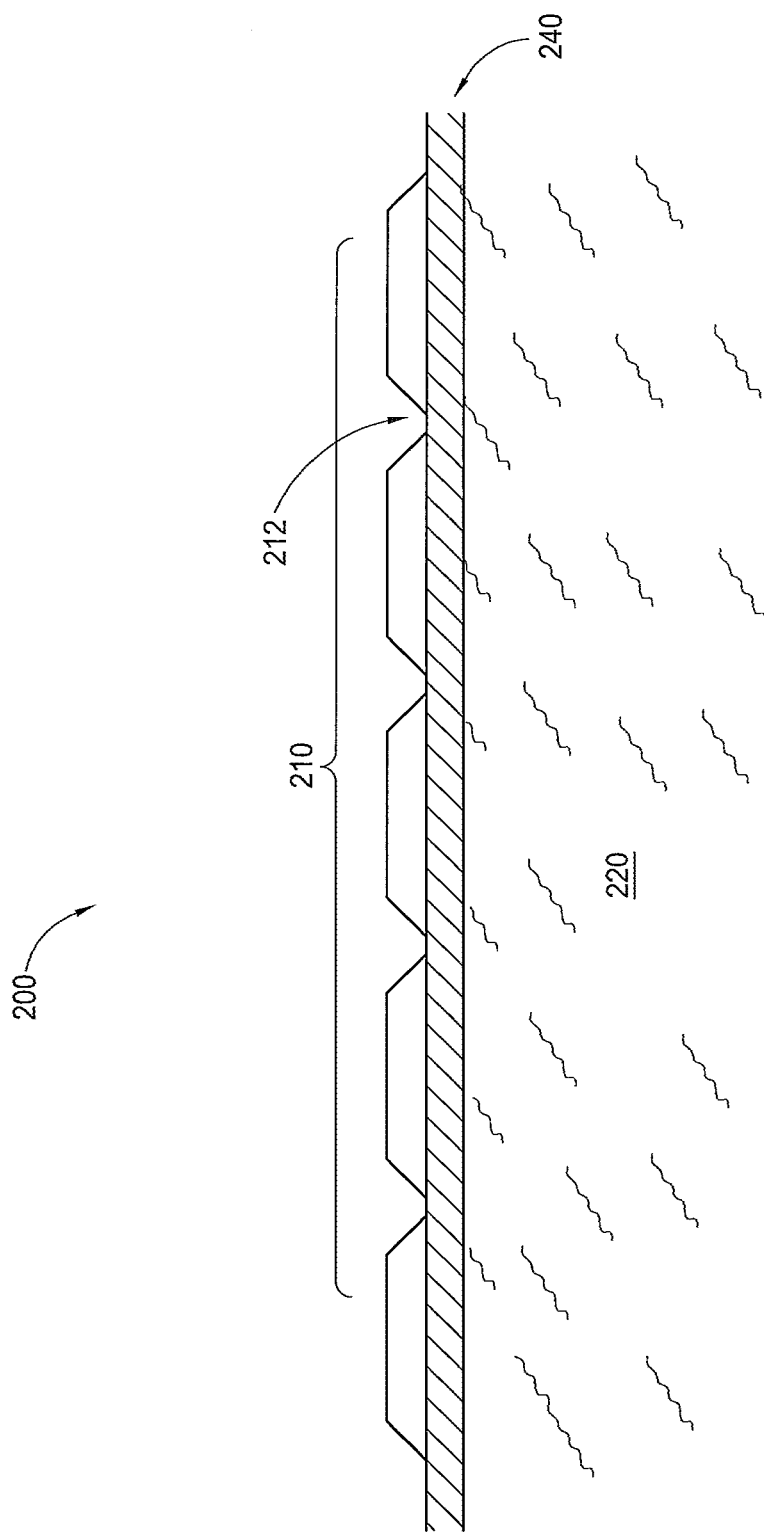
FIG. 3E schematically illustrates an example target comprising a plurality of structures separated from one another by a plurality of recesses in accordance with certain embodiments described herein.

FIG. 3E schematically illustrates an example target 200 comprising a plurality of structures 210 separated from one another by a plurality of recesses 212 in accordance with certain embodiments described herein. The recesses 212 (e.g., notches) are configured to allow the structures 210 to undergo thermal expansion without delamination from the substrate 220. The target 200 of FIG. 3E further comprises a layer 240 between the x-ray generating material and the substrate 220 (e.g., comprising a diffusion-inhibiting material, a material configured to improve adhesion of the structure 210 to the substrate 220, and/or a material configured to improve the thermal conductance between the structure 210 and the substrate 220).

X-Ray Optical System

In certain embodiments, the generated x-rays diverge from the x-ray source 110 and the x-ray optical system 120 comprises at least one x-ray optical train 300 downstream of the x-ray source 110. The at least one x-ray optical train 300 of certain embodiments is configured to collect a portion of the generated x-rays and to direct at least some of the collected x-rays towards the sample 130 (e.g., by collimating and/or focusing the collected x-rays). In certain embodiments in which the x-ray optical system 120 is configured to focus the x-rays, the point spread function (PSF) of the at least one optical train 300 is sufficiently small such that the spot size at the focus of the at least one optical train 300 is less than or equal to 500 microns (e.g., 50 microns or less) and the at least one optical train 300 has a working distance greater than 10 mm (e.g., in a range of 10 mm to 30 mm) at the focal spot 302 of the at least one optical train 300. In certain embodiments, the at least one x-ray optical train 300 comprises at least one reflective x-ray optic 310 configured to collect and focus x-ray energies of a bandwidth greater than 0.1% of an x-ray energy of interest. Various x-ray optical systems, x-ray optical trains, and x-ray optics compatible with certain embodiments described herein are described in U.S. Pat. Nos. 9,570,265 and 9,449,781 and U.S. Publ. Appl. Nos. 2017/0162288 and 2019/0088381, each of which is hereby incorporated by reference in its entirety.

In certain embodiments, the at least one optical train 300 comprises at least one x-ray optic 310 (e.g. at least one capillary x-ray optic; capillary tube) with axial symmetry and aligned along an axis of brightest illumination from the x-ray source 110. The at least one x-ray optic 310 of certain embodiments is configured to reflect at least some of the collected x-rays 230 at grazing angles, focusing a portion of the x-rays into a focused x-ray beam 320 onto a focal spot 302. For example, at least one capillary x-ray optic can comprise an inner surface profile that corresponds to one or more portions of a quadric function, such as an ellipsoid, paraboloid, hyperboloid, cylindrical (e.g., two-dimensional) versions of these quadric functions, or Wolter Type I optics (paraboloid and ellipsoid/hyperboloid). In certain other embodiments, the at least one optical train 300 can comprise alternative focusing x-ray optics 310, including but not limited to: conical, polycapillary optics, Kirkpatrick-Baez optics, and Montel mirror. In certain embodiments, the at least one optical train 300 further comprises other x-ray optical elements, including but not limited to: Fresnel zone plates, cylindrical Wolter optics, Wolter Type II or III optics, Schwarzschild optics, diffraction gratings, crystal mirrors using Bragg diffraction, hole-array lenses, multi-prism or "alligator" lenses, rolled x-ray prism lenses, "lobster eye" optics, micro channel plate optics.

In certain embodiments, the at least one x-ray optic 310 comprises an optical substrite material, examples of which include but are not limited to: glass, silica, quartz, BK7, silicon (Si), ultra-low expansion glass (e.g., ULE® glass available from Corning Inc. of Corning N.Y.; Zerodur® glass ceramic available from Schott AG of Mainz Germany), or other elemental materials. In certain embodiments, the at least one x-ray optic 310 comprises at least one coating configured to improve the reflectivity of the at least one x-ray optic 310. For example, the at least one coating can comprise an elemental or alloy coating having a critical angle for total external reflection, which occurs for angles of incidence smaller than the critical angle. The elemental or alloy coating can comprise one or more high atomic elements (e.g. elements having an atomic number greater than 26; elements having a mass density greater than 2.5 g/cm$^3$; platinum; gold; silver) and can be at least 25 nm thick.

For another example, the at least one coating can comprise a multilayer coating comprising alternating periodic layers of two or more materials that provide constructive interference in reflection for certain x-ray wavelengths. The reflection efficiency of such multilayer coatings depends on the wavelength and the angle of incidence of the x-rays, as well as the thickness of the alternating layers, so such multilayer coatings can be used as a narrow energy band reflector. Examples of materials for the alternating layers include but are not limited to: tungsten/carbon (W/C), tungsten/silicon (W/Si), tungsten/tungsten silicide (W/WSi$_2$), molybdenum/silicon (Mo/Si), nickel/carbon (Ni/C), chromium/scandium (Cr/Sc), lanthanum/boron carbide (La/B$_4$C), tungsten/boron carbide (W/B$_4$C), and tantalum/silicon (Ta/Si).

In certain embodiments, the at least one x-ray optic 310 comprises at least one surface configured to be illuminated by the x-rays at a near-grazing angle (e.g. at angles of 5 degrees or smaller relative to the surface) which exceeds the critical angle for reflection such that reflection of higher energy x-rays by the surface is attenuated (e.g., a "high-energy cutoff" for reflection, which is well defined for a given material and critical angle). In certain embodiments, the attenuation of high energy x-rays prevents spurious signals due to higher harmonics (e.g. twice the energy) from being observed downstream in the x-ray detector 150. For example, the at least one surface and the near-grazing angle can be configured to reduce reflection of x-rays having energies more than 1.2 times the "high-energy cutoff" to be below 30%, below 25%, or below 10%. In certain embodiments, the attenuation of reflected high energy x-rays enables the x-ray source 110 to be operated at higher accelerating voltages that significantly increase efficient generation of bremsstrahlung radiation (e.g., the at least one x-ray optic 310 rejecting x-rays with energies corresponding to the higher-order harmonics of the crystal analyzer, thereby achieving higher signal-to-noise ratios by reducing higher-order contamination).

Figure 4A:
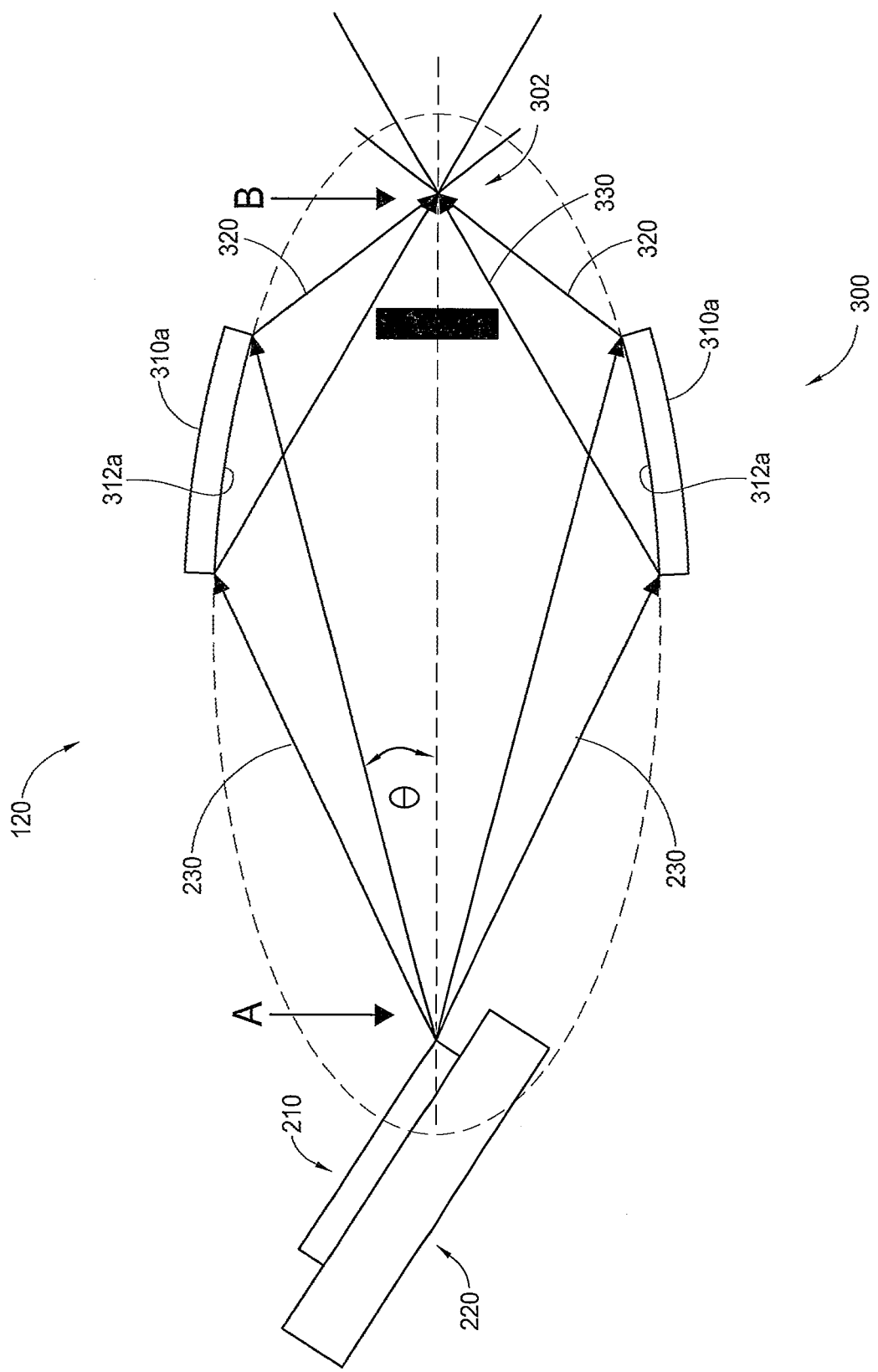
FIG. 4A schematically illustrates a cross-sectional view of an example optical train comprising an ellipsoidal optic in accordance with certain embodiments described herein.

FIG. 4A schematically illustrates a cross-sectional view of an example optical train 300 comprising an ellipsoidal optic 301a having a surface 312 that corresponds to a portion of an ellipsoid (indicated by the dashed line of FIG. 4A) in accordance with certain embodiments described herein. The ellipsoidal optic 310a of certain embodiments comprises a capillary optic that is axially symmetric and has an inner surface 312 that corresponds to a portion of an ellipsoid. The ellipsoidal optic 310a has two foci (labeled A and B in FIG. 4A) such that x-rays radiating from one of the two foci and irradiating the surface 312 will be reflected and converge onto the other of the two foci. As schematically illustrated in FIG. 4A, some of the diverging x-rays emitted from the x-ray generating structure 210 at the focus A of the ellipse irradiate the surface 312 of the ellipsoidal optic 310a, undergo total external reflection from the surface 312 of the ellipsoidal optic 310a, and are focused onto the second focus B (e.g., the focal spot 302).

Figure 4B:
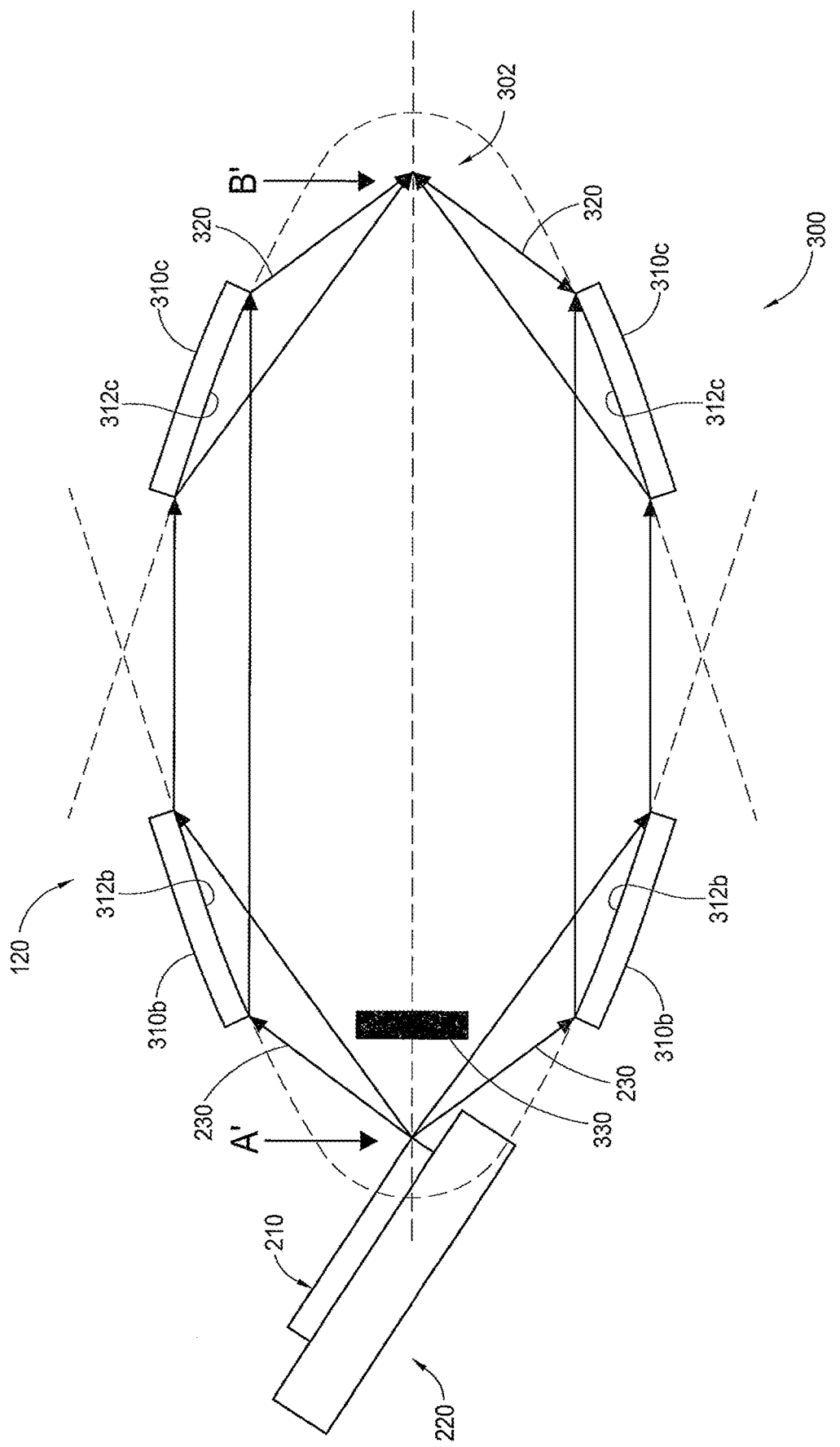
FIG. 4B schematically illustrates a cross-sectional view of an example optical train comprising two paraboloidal optics in accordance with certain embodiments described herein.

FIG. 4B schematically illustrates a cross-sectional view of an example optical train 300 comprising two paraboloidal optics 310b, 310c, each having a surface 312b, 312c that corresponds to a portions of a paraboloid (indicated by the dashed line in FIG. 4B) in accordance with certain embodiments described herein. The two paraboloidal optics 310b, 310c of certain embodiments comprise a single capillary optic that is axially symmetric, while the two paraboloidal optics 310b, 310c of certain other embodiments comprise two different capillary optics, each of which is axially symmetric, positioned with its symmetry axis aligned with the symmetry axis of the other capillary optic, and having an inner surface 312b, 312c that corresponds to a portion of one of the two paraboloids. The paraboloidal optic 310b has a corresponding focus (labeled A' in FIG. 4B) such that x-rays radiating from the focus A' and irradiating the inner surface 312b of the paraboloidal optic 312b undergo total external reflection from the inner surface 312b and are collimated (e.g., form a collimated x-ray beam). The paraboloidal optic 310c has a corresponding focus (labeled B' in FIG. 4B) such that the collimated x-rays from the paraboloidal optic 310b that irradiate the inner surface 312c of the paraboloidal optic 310c undergo total external reflection from the inner surface 312c and are focused onto the second focus B' (e.g., the focal spot 302). Although FIG. 4B shows the two paraboloidal optics 310b, 310c having the same dimensions, curvatures, and relative focus positions, the two paraboloidal optics 310b, 310c of certain embodiments have different dimensions, curvatures, and/or relative focus positions.

In certain embodiments, as schematically illustrated by FIGS. 4A and 4B, the x-ray optic 310 is placed so that it collects x-rays at a take-off angle θ from the x-ray target 200 (e.g., relative to the local surface of the x-ray generating structure 210) that is less than 30 degrees, less than 15 degrees (e.g., 11.5 degrees or about 200 mrad), or less than 6 degrees (e.g., 0 to 105 mrad). In certain embodiments, a beam stop 330 is configured to stop (e.g., intercept) x-rays that are propagating along the axis of the x-ray optics but do not irradiate the inner surface of the x-ray optics. The beam stop 330 of certain embodiments defines a cone angle (e.g., less than 3 degrees; less than 50 mrad) centered around the take-off angle θ of the x-rays (e.g., from the x-ray source 110). As schematically illustrated by FIG. 4A, the beam stop 330 can be positioned at the exit side of the x-ray optic, and as schematically illustrated by FIG. 4B, the beam stop 330 can be positioned at the entrance side of the x-ray optic. In certain embodiments with a single condenser optic, the x-ray optical system 120 comprises a beam stop 330 on the entrance side of the condenser optic and a beam stop 330 on the exit side of the condenser optic, with the exit-side beam stop 330 being about two-thirds the size of the entrance-side beam stop 330. Both of these beam stops 330 can be configured to block the through-beam (e.g., x-rays not reflected by the condenser optic), and the exit-side beam stop 330 can be further configured to block scattered x-rays from the x-ray optic 310.

While both FIGS. 4A and 4B schematically illustrate the x-rays being emitted from a single point on the x-ray generating structure 210 for the purpose of simplicity, x-rays can be generated by other portions of the x-ray generating structure 210. In certain embodiments, the x-ray optical system 120 further comprises at least one aperture 340 configured to attenuate the background contribution from scattered x-rays, thereby helping to improve the signal-to-background ratio of the system. The at least one x-ray optic 310 can be configured to produce a focused x-ray beam 320 and an aperture 340 can be placed in the same plane as the focal plane of the at least one x-ray optical train 300. For example, an aperture 340 can be coincident with the focal spot 302 of the x-ray optic 310 (e.g., focus B of FIG. 4A; focus B' of FIG. 4B). The at least one aperture 340 can comprise a hole or slit in a metal sheet (e.g., molybdenum; platinum) having a thickness (e.g., 20 microns) that is shorter than a depth of focus of the optical train 300, the hole or slit having a size comparable to the size of the focused x-ray beam 320 (e.g., diameter or width in a range of 5 to 25 microns). In certain embodiments, the x-ray optical system 120 further comprises at least one filter (e.g., to reduce background at the energies of interest arising from elastic scattering and to enhance sensitivity). Example filters compatible with certain embodiments described herein include but are not limited to: notch filters, Bragg filters (e.g., using a thin mosaic crystal or single crystal), and absorption filters (e.g., a sheet or layer of aluminum) configured to be irradiated by the x-rays and to further attenuate x-rays above the absorption edge of the filter material while not appreciably affecting x-rays with energies below the absorption edge.

In certain embodiments, the x-ray optical system 120 is matched to one or more x-ray generating materials of the x-ray generating structures 210 of the x-ray source 110 (e.g., by including x-ray optics 310 that have geometric shapes, sizes, and surface coatings that collect as many x-rays as possible from the x-ray source 110 and at an angle that satisfies the critical reflection angle of the x-ray energies of interest from the x-ray source 110; by maximizing the numerical aperture of the x-ray optics 310 for the x-ray energies of interest). For example, as schematically illustrated by FIG. 1B, in certain embodiments in which the at least one x-ray source 110 comprises multiple x-ray sources 110a, 110b, 110c (e.g., each comprising at least one x-ray generating structure 210 with at least one x-ray generating material), multiple optical trains 300a, 300b, 300c can be used, with each optical train 300a, 300b, 300c matched to a selected characteristic x-ray energy of the x-ray generating material of the corresponding x-ray source 110a, 110b, 110c. In certain other embodiments in which a single x-ray source 110 comprises multiple x-ray generating structures 210 with different x-ray generating materials, multiple interchangeable optical trains 300 can be used, with each optical train 300 matched to a selected characteristic x-ray energy of the x-ray generating material of the corresponding x-ray generating structure 210. An x-ray generating material of an x-ray generating structure 210 and an optical train 300 can be considered "matched" as used herein when the cutoff energy of the optical train 300 is above a strong characteristic line of the x-ray generating material and when the optical train 300 is configured to optimize reflection of the selected characteristic line. In certain embodiments, the multiple interchangeable optical trains 300 are held on a mount configured to translate (e.g., move laterally) and/or to rotate the optical trains 300 so that a selected optical train 300 receives the x-rays 230 emitted from the x-ray source 110.

Sample

In certain embodiments, the sample 130 to be examined is mechanically coupled to a mount 400 and is positioned such that the focused x-ray beam 320 irradiates the sample 130 (e.g., the focal spot 302 of the x-ray optical system 120 is coincident with the sample 130). The mount 400 is configured to translate and/or to rotate the sample 130 so that different portions of the sample 130 are illuminated by the converging x-rays of the focused x-ray beam 320 (e.g., allowing different positions on the sample 130 to be illuminated in a systematic scan or from several angles of incidence) with the translation and/or rotation controlled by a controller (e.g., the analysis system 170).

X-Ray Spectrometer

In certain embodiments, the x-ray spectrometer 140 is configured to collect and analyze the fluorescence x-rays 410 emitted from the sample 130 (e.g., from a secondary x-ray source corresponding to the focal spot 302 of the at least one x-ray optical train 300) and their energies. In certain embodiments, the x-ray spectrometer 140 comprises at least one x-ray analyzer 160 configured to disperse the fluorescence x-rays 410 and at least one x-ray detector 150 (e.g., array detector) configured to record the intensity of the dispersed x-rays as a function of position.

For example, as schematically illustrated by FIGS. 1A and 1B, the at least one x-ray analyzer 160 is irradiated by x-rays emitted from the sample 130, and diffracts x-rays of different wavelengths $\lambda_1, \ldots, \mu_N$ to different locations on a spatially-resolving x-ray detector 150. In this way, the x-ray analyzer 160 acts as a Bragg diffraction element and x-rays that are not diffracted are transmitted through the x-ray analyzer 160 and absorbed by a beam stop (not shown).

In certain embodiments, the at least one x-ray analyzer 160 comprises at least one single crystal or mosaic crystal having a width (e.g., in the sagittal plane) greater than or equal to 20 mm (e.g., 20 mm to 50 mm; 50 mm) and a length (e.g., in the dispersion plane) greater than or equal to 50 mm (e.g., 50 mm to 100 mm; 50 mm to 200 mm; 200 mm) and positioned in a range of 100 mm to 2000 mm (e.g., 250 mm) away from the source of x-rays (e.g., the sample 130). Examples of materials for the at least one x-ray analyzer 160 compatible with certain embodiments described herein include but are not limited to: Quartz (10-10) (e.g., for spectral range of 1.6 keV to 2 keV), Quartz (11-20) (e.g., for spectral range of 2.8 keV to 3.5 keV), Si (111) (e.g., for spectral range of 2 keV to 2.8 keV), Si (220) (e.g., for spectral range of 3.3 keV to 5 keV), Si (311), Si (511), Si (400), Si (620), InSb (111), Ge (111), Ge (220), Ge (311), Ge (511), Ge (400), Ge (620), and graphite layers (e.g., between 15 and 200 microns thick grown onto a curved substrate)

aligned along the 002 plane, such as highly oriented pyrolytic graphite (HOPG), or highly annealed pyrolytic graphite (HAPG).

In certain embodiments, the at least one x-ray analyzer 160 can comprise a single planar Bragg crystal, a crystal curved in one plane (e.g., the dispersion plane; the sagittal plane) and flat in the other perpendicular plane, and/or a doubly curved crystal curved in two perpendicular planes (e.g., the dispersion plane and the sagittal plane). For example, the at least one x-ray analyzer 160 can comprise a curved single-crystal portion of a wafer (e.g., single-crystal silicon aligned with the surface along the 111 or the 220 planes). For another example, the at least one x-ray analyzer 160 can comprise a single crystal grown onto a curved substrate, or thinned from a previously grown wafers and bent. In certain embodiments, the at least one x-ray analyzer 160 comprises a mosaic crystal comprising an ensemble of micro-crystals at varied angles throughout the material, each as small as a few hundred nanometers or as large as several microns, held by a backing material (e.g., metal). The mosaic crystal of certain embodiments can be curved at least in the sagittal, non-dispersive direction. X-rays that are not diffracted by the micro-crystal at the surface can still be diffracted from another micro-crystal positioned deeper within the mosaic crystal.

In certain embodiments, the crystal can be curved to allow the x-rays diverging in the directions perpendicular to the direction of propagation to be focused onto the x-ray detector 150 (e.g., von Hamos spectrometer). In certain embodiments, the crystal Bragg planes are curved with a bending radius in a range between 50 mm and 200 mm and/or with at least twice the radius of the Rowland circle 500 in the dispersion plane (e.g., Johann geometry; Johansson geometry). In certain other embodiments, the x-ray spectrometer 140 is arranged in the Wittry geometry with a doubly curved crystal (e.g., a Wittry crystal having the doubly curved crystal surface with the same radius as the Rowland circle 500 in the dispersion plane, twice the radius of the Rowland circle 500 in the sagittal plane, and the crystal Bragg planes are curved to a radius equal to twice the radius of the Rowland circle 500 in both planes). In certain such embodiments, the Wittry geometry advantageously reduces (e.g., eliminates) geometrical spectral broadening resulting in a worsening of the energy resolution (e.g., as compared to the Johann geometry) and/or advantageously increases the efficiency of collection of fluorescence x-rays for fast XES measurements over a wide range of Bragg angles. In certain other embodiments, other doubly curved crystal geometries can be used (e.g., over limited angular ranges), including but not limited to: spherical Johann geometry, toroidal Johann geometry, and spherical Johansson geometry.

Figure 5:
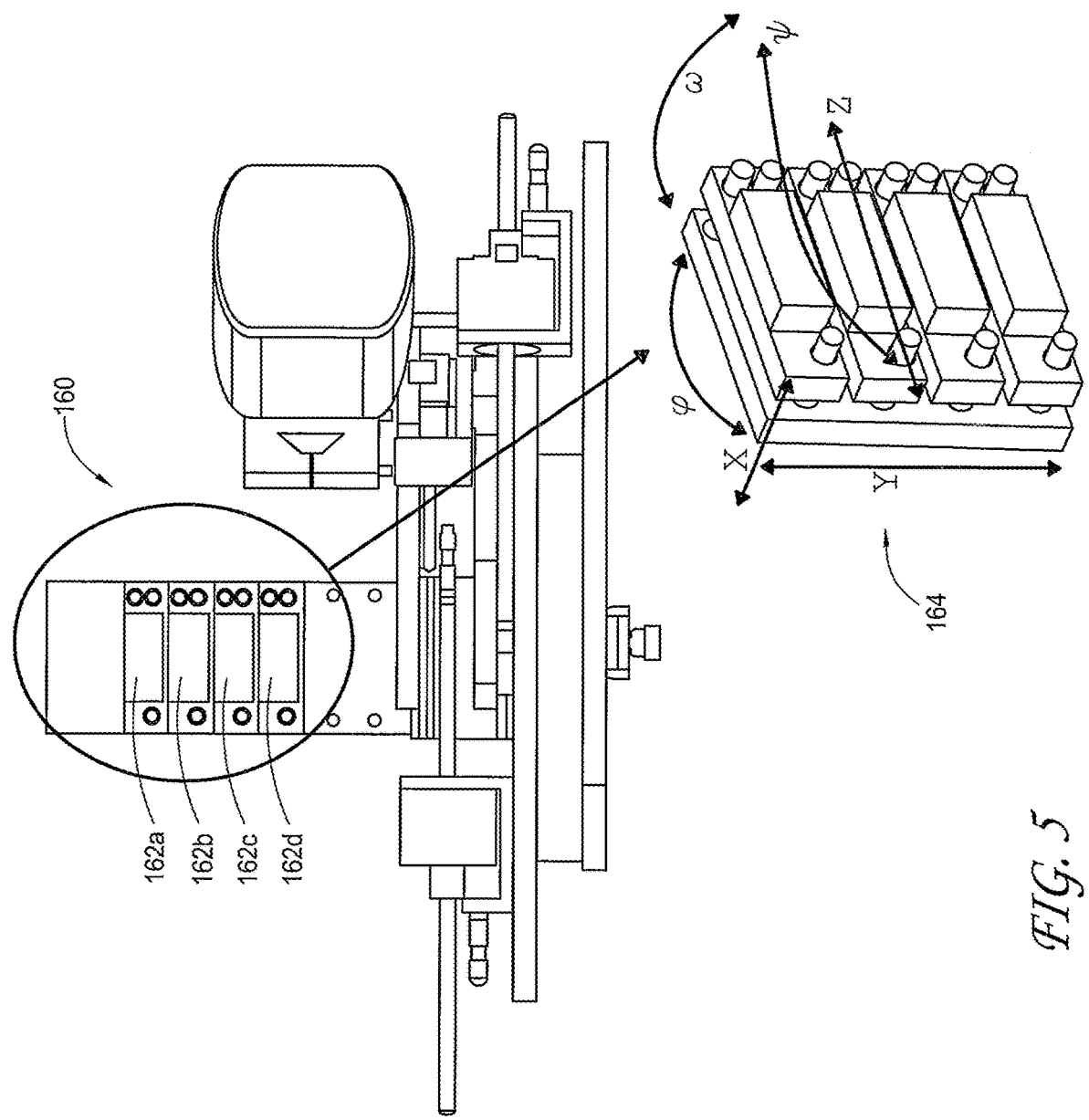
FIG. 5 schematically illustrates an example x-ray analyzer comprising multiple crystals that are configured to be interchanged with one another in accordance with certain embodiments described herein.

FIG. 5 schematically illustrates an example x-ray analyzer 160 comprising multiple crystals 162 that are configured to be interchanged with one another in accordance with certain embodiments described herein. As shown in FIG. 5, the x-ray analyzer 160 comprise multiple crystals 162a, 162b, 162c, 162d (e.g., multiple doubly curved crystals) mounted on a stage 164 configured to move linearly in three perpendicular directions (e.g., X, Y, and Z) to select an appropriate crystal 162 to receive the fluorescence x-rays 140 and to independently adjust an orientation of each crystal 162 (e.g., pitch, roll, and yaw), thereby providing six degrees of motion for precise adjustment (e.g., for optimizing throughput and energy resolution).

In certain embodiments, the x-ray detector 150 comprises a spatially-resolving detector (e.g., a position-sensitive detector, a CCD-based detector comprising a two-dimensional or one-dimensional array sensor). For example, the x-ray detector 150 can comprise a pixel array having at least 1000 pixels in a first direction (e.g., in the dispersion plane) and at least 100 pixels in a second direction perpendicular to the first direction (e.g., a 2048×256 pixel array; 1024×1024 pixel array; 2048×512 pixel array; 2048×2048 pixel array). In certain embodiments, the long axis of the pixel array is aligned along the direction of x-ray propagation, and the dispersion of x-rays by wavelength occurs along the long axis. In certain embodiments, the x-ray detector 150 includes one or more detector elements of any type that detects x-rays, including but not limited to: linear detector elements, Si-PIN photodiode elements, proportional detector elements, avalanche detector elements, scintillator-type elements, gas-filled array elements, energy-dispersive detector elements, CMOS detector elements, S-CMOS detector elements, CCD detector elements (e.g., direct detection CCD with a sufficiently high detection quantum efficiency (DQE) and/or fast readout speed configured to serve as an energy-resolving detector).

In certain embodiments, the x-ray detector 150 is positioned to have its center pixel tangent to the Rowland circle 500. In certain embodiments, the x-ray detector 150 is configured to provide high spatial resolution with pixel sizes (e.g., widths) less than 75 microns (e.g., in a range of 3 microns to 26 microns; in a range of less than or equal to 20 microns; in a range of 15 microns to 20 microns). For example, the x-ray detector 150 can have multi-frame readout and sufficiently small pixels configured to provide pixel resolution of less than 0.3 eV (e.g., less than 0.1 eV).

In certain embodiments, the x-ray detector 150 comprises one or more filters (e.g., thin foils) positioned between the sample 130 and the x-ray detector 150 to select a certain portion of the x-rays emerging from the sample 130 for detection. In certain embodiments, the x-ray spectrometer 140 further comprises a second detector configured to detect the intensity of the incident x-rays, allowing normalization of the transmitted signal with any variations in the incident x-ray intensity. In certain embodiments, the x-ray spectrometer 140 comprises one or more apertures configured to prevent unwanted x-rays from being detected.

X-Ray Emission Spectroscopy Configurations

Figure 6:
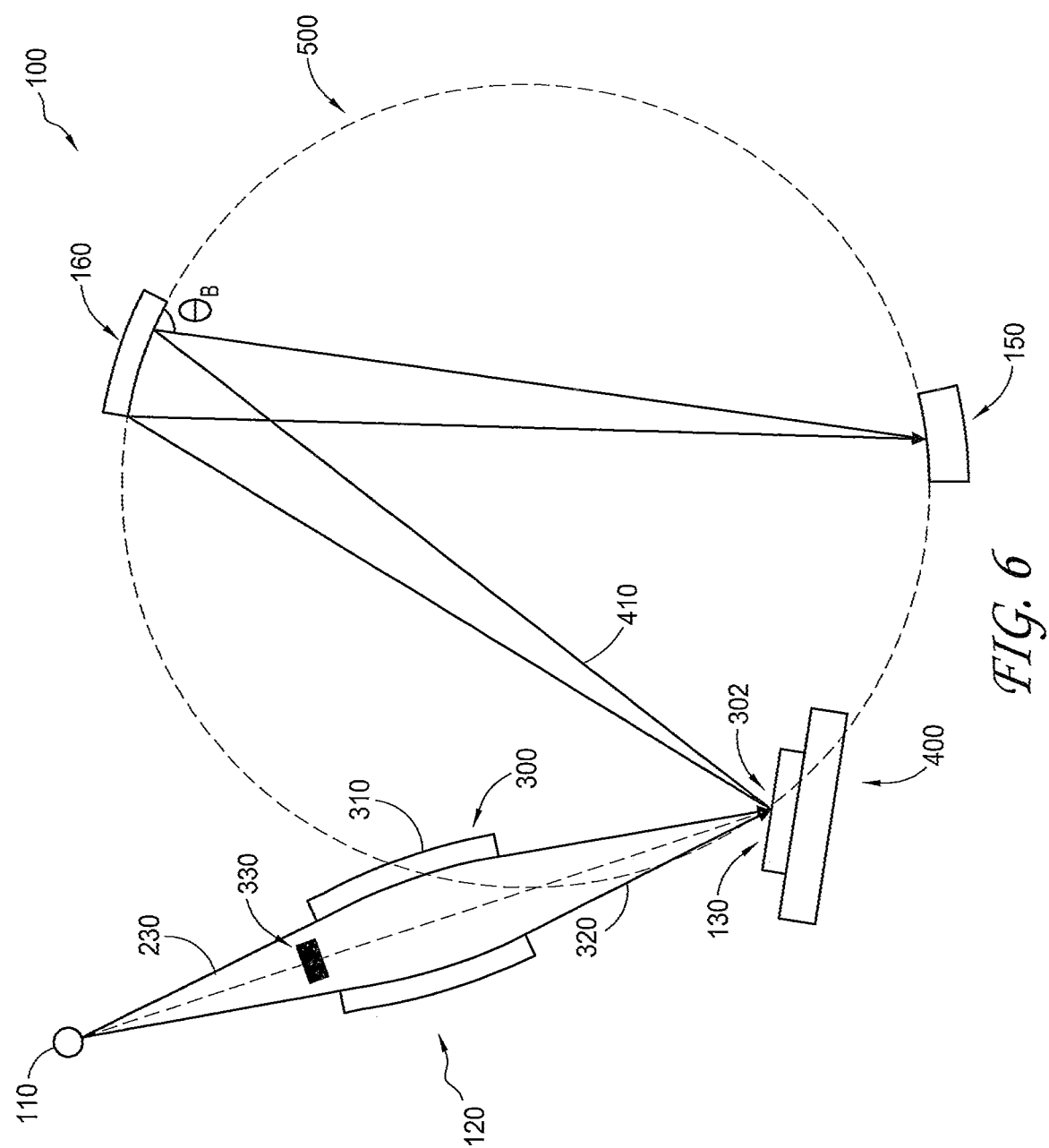
FIG. 6 schematically illustrates an example x-ray spectrometer system having an "on-Rowland circle" geometry in accordance with certain embodiments described herein.

FIG. 6 schematically illustrates an example x-ray spectrometer system 100 having an "on-Rowland circle" geometry in accordance with certain embodiments described herein. As used herein, the phrase "'on-Rowland circle' geometry" has its broadest reasonable interpretation, including but not limited to an arrangement in which a localized region comprising the fluorescence x-rays 410 (e.g., the focal spot 302 at which the sample 130 is irradiated by the focused x-rays 320 from the x-ray source 110; the location at which the focused x-rays 320 impinge the sample 130; the focal spot 302 at which an optical train 300 focuses the fluorescence x-rays 320 emitted from the sample 130), the x-ray analyzer 160 (e.g., curved with a radius of curvature that is twice the radius of the Rowland circle 500), and the x-ray detector 150 each lie on the Rowland circle 500. In certain such embodiments, the spectral lines of the fluorescence x-rays 410 are focused by the x-ray analyzer 160 onto the x-ray detector 150.

For example, as schematically illustrated by FIG. 6, the x-ray spectrometer system 100 comprises an x-ray source 110 configured to emit x-rays that are collected and focused by an x-ray optical system 120 comprising an optical train 300 (e.g., comprising an axially symmetric capillary optic 310) and a central beam stop 330, the x-ray optical system 120 configured to focus the x-rays into a focused x-ray beam 320 onto a focal spot 302 of the x-ray optical system 120. The sample 130 is mounted to a mount 400 that is configured to controllably move (e.g., translate; rotate) the sample 130 such that a region of interest of the sample 130 is coincident with the focal spot 302. Under illumination by the focused x-ray beam 320, the region of interest of the sample 130 produces fluorescence x-rays 410. The x-ray analyzer 160 (e.g., curved to Johansson geometry, curved to Johann geometry) collects and diffracts at least some of the fluorescence x-rays 410 toward the x-ray detector 150. The sample 130, the x-ray analyzer 160, and the x-ray detector 150 are each located on the Rowland circle 500 such that the x-ray detector 150 detects a narrow band of x-rays (e.g., x-rays having a single x-ray wavelength; x-rays having energies within a bandwidth less than 50 eV, less than 20 eV, or less than 10 eV). For example, the x-ray spectrometer system 100 of FIG. 6 can be configured to monitor shifts of x-ray lines (e.g., x-ray peak energies).

In certain such embodiments, the x-ray source 110 comprises a plurality of x-ray generating structures 210 with different x-ray generating materials and the x-ray optical system 120 comprises a plurality of optical trains 300 (each optical train 300 matched or optimized for use with one of the x-ray generating materials) configured to collect x-rays in a sequence of spectral bands (e.g., combinations for different 1 keV bands). In certain embodiments, the x-ray analyzer 160 is configured to be rotated to expand the range of x-ray energies or wavelengths of the x-rays diffracted towards the x-ray detector 150 for a single combination of x-ray source 110 and x-ray optical system 120.

The x-ray spectrometer system 100 schematically illustrated by FIGS. 1A and 1B has an "off-Rowland circle" geometry in accordance with certain embodiments described herein. As used herein, the phrase "'off-Rowland circle' geometry" has its broadest reasonable interpretation, including but not limited to an arrangement in which a localized region comprising the fluorescence x-rays 410 (e.g., the focal spot 302 at which the sample 130 is irradiated by the focused x-rays 320 from the x-ray source 110; the location at which the focused x-ray beam 320 impinges the sample 130; the focal spot 302 at which an optical train 300 focuses the fluorescence x-rays 320 emitted from the sample 130) is within (e.g., off or not on) the Rowland circle 500 and the x-ray analyzer 160 (e.g., curved with a radius of curvature that is twice the radius of the Rowland circle 500) and the x-ray detector 150 each lie on the Rowland circle 500. In certain such embodiments, the bandwidth of the collected x-rays is broadened as compared to an "on-Rowland circle" geometry (e.g., the "off-Rowland circle" geometry can provide a small collection angle but a wide energy coverage while the "on-Rowland circle" geometry can provide a large collection angle but a narrow energy coverage). In addition, for an x-ray spectrometer system 100 having an "off-Rowland circle" geometry, x-rays having different wavelengths (e.g., x-rays with wavelengths $\lambda_1$ and $\lambda_2$, as shown in FIGS. 1A and 1B) are diffracted towards different regions by the x-ray analyzer 160 on the Rowland circle 500 and a spatially-resolving x-ray detector 150 on the Rowland circle 500 is able to distinguish between the x-rays having different wavelengths which impinge the different regions of the x-ray detector 150.

In certain embodiments, the "off-Rowland circle" geometry provides a decrease of efficiency for a single wavelength while providing the ability to simultaneously detect multiple x-ray wavelengths (e.g., corresponding to different atomic elements within the sample 130). In certain embodiments, the sample 130 is moved relative to the focal spot 302 of the focused x-ray beam 320 for one-dimensional or two-dimensional mapping of the sample 130 (e.g., with spatial resolution better than or equal to 500 microns (e.g., better than or equal to 200 microns; better than or equal to 100 microns; better than or equal to 50 microns). In certain embodiments, as schematically illustrated by FIG. 1B, while the location at which the focused x-ray beams 320 impinge the sample 130 is within the Rowland circle 500, an apparent source of fluorescence x-rays 410 (e.g., an apparent focal spot from which the fluorescence x-rays 410 received by the x-ray analyzer 160 appear to be emitted) is on the Rowland circle 500.

Figure 7:
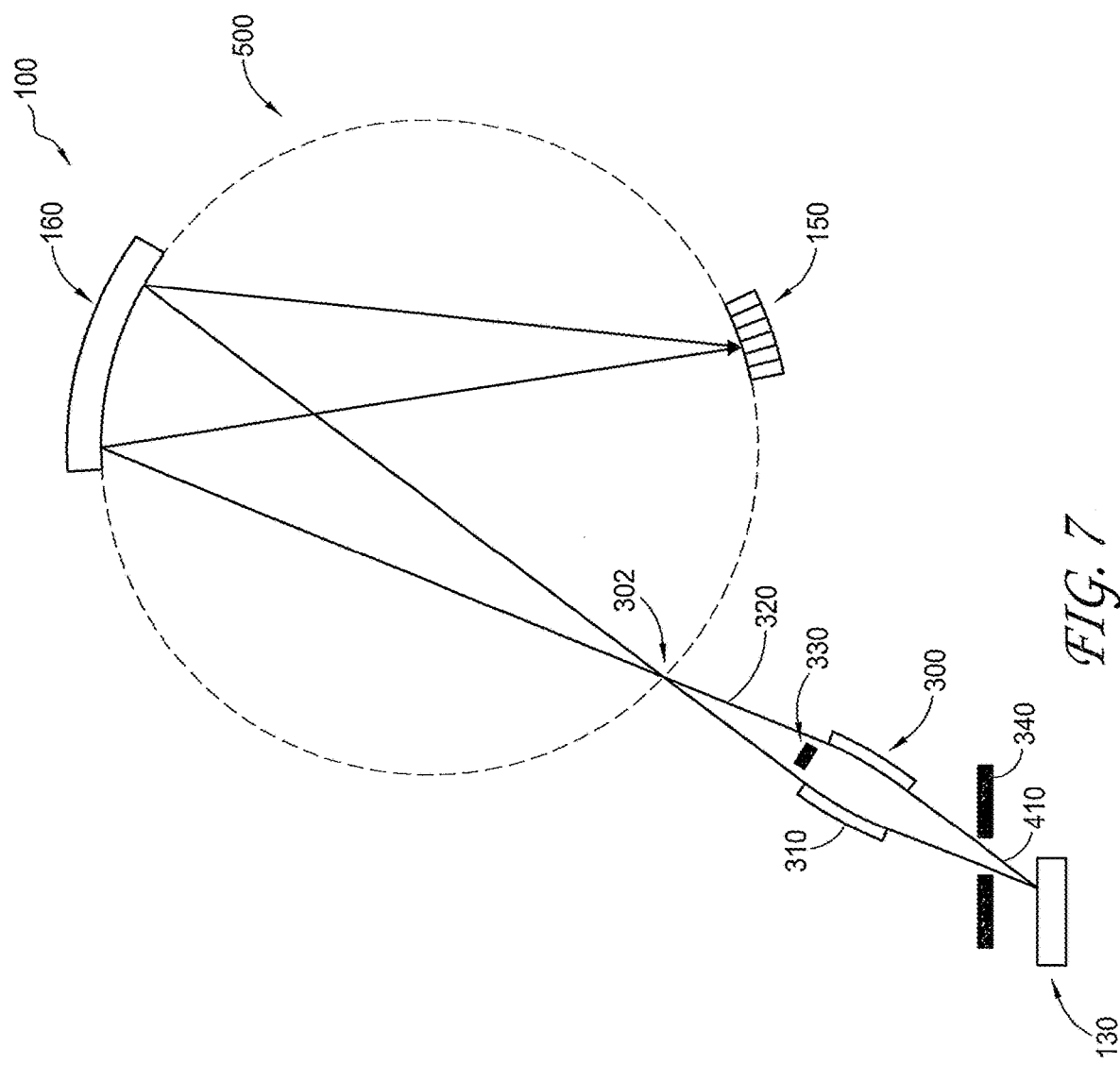
FIG. 7 schematically illustrates an example x-ray spectrometer system having an x-ray optical train configured to receive fluorescence x-rays from the sample in accordance with certain embodiments described herein.

FIG. 7 schematically illustrates an example x-ray spectrometer system 100 having an x-ray optical train 300 configured to receive fluorescence x-rays 410 from the sample 130 in accordance with certain embodiments described herein. In contrast to x-ray optical trains 300 that receive x-rays from an x-ray source 110, as described herein, the x-ray optical train 300 of the x-ray spectrometer system 100 of FIG. 7 is on the detection side (e.g., configured to receive fluorescence x-rays 410 emitted from the sample 130). The x-ray optical train 300 of the x-ray spectrometer system 100 of FIG. 7 can include at least one x-ray optic 310, at least one beam stop 330, and/or at least one aperture 340 as described herein for x-ray optical trains 300 configured to receive x-rays from an x-ray source 110. For example, as schematically illustrated by FIG. 7, a beam stop 330 can be configured to remove fluorescence x-rays 410 that are not reflected by the x-ray optical train 300 from reaching the x-ray analyzer 160 and/or an aperture 340 can be placed downstream of the sample 130.

As schematically illustrated by FIG. 7, the fluorescence x-rays 410 are collected by the x-ray optical train 300 and are focused onto a focal spot 302 on the Rowland circle 500. The focal spot 302 serves as an apparent source of x-rays for the x-ray analyzer 160 and the x-ray detector 150, both of which are on the Rowland circle 500. While the x-ray spectrometer system 100 schematically illustrated by FIG. 7 has an "on-Rowland circle" geometry in which each of the focal spot 302, x-ray analyzer 160, and x-ray detector 150 is on the Rowland circle 500, in certain other embodiments, the x-ray spectrometer system 100 has an "off-Rowland circle" geometry in which the focal spot 302 is positioned within the Rowland circle 500 and the x-ray analyzer 160 and the spatially-resolving x-ray detector 150 are on the Rowland circle 500 for simultaneous detection of multiple x-ray energies.

In certain embodiments, the fluorescence x-rays 410 are generated by electron bombardment of the sample 130, while in certain other embodiments, the fluorescence x-rays 410 are generated by x-ray illumination of the sample 130 (e.g., by an x-ray source 110 and an x-ray optical system 120 as described herein). For example, the fluorescence x-rays 410 can be generated by irradiation of the sample 130 by focused x-rays from the x-ray optical system 120, and analysis of the fluorescence x-rays 410 can provide confocal information.

Figure 8:
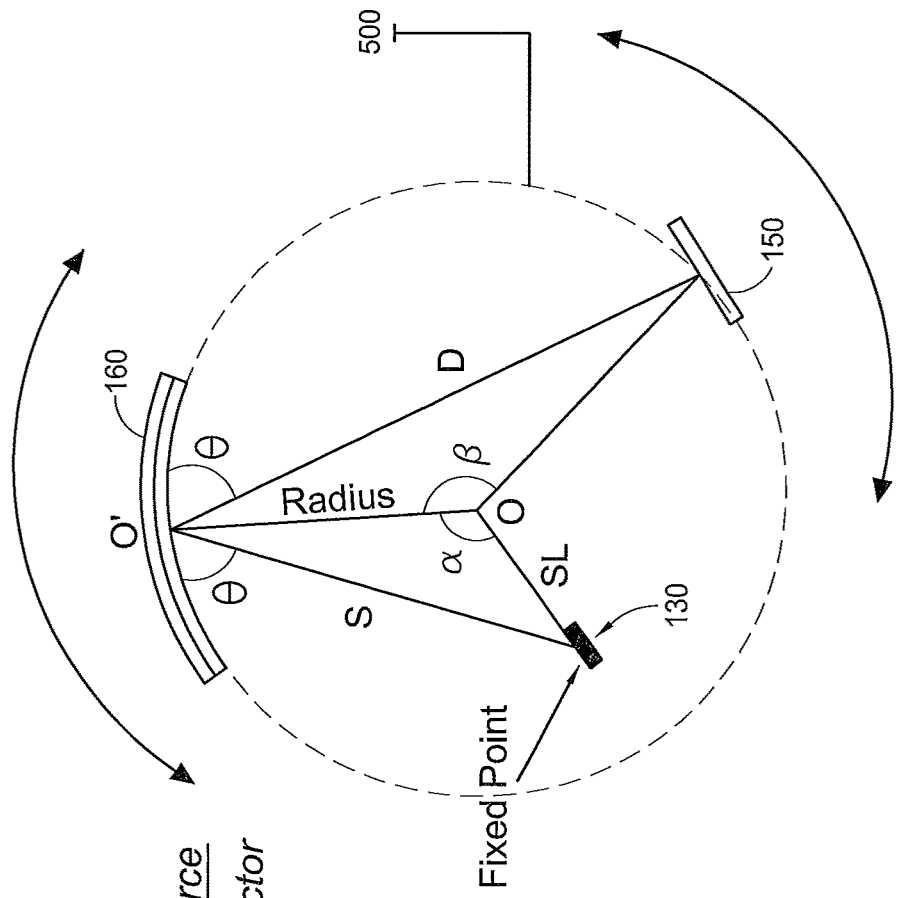
FIG. 8 schematically illustrates an example calculation of the distance from the x-ray analyzer to the sample in accordance with certain embodiments described herein.

FIG. 8 schematically illustrates an example calculation of the distance from the x-ray analyzer 160 to the sample 130 in accordance with certain embodiments described herein. In certain embodiments, the distance S from the x-ray analyzer 160 to the sample 130 is set using the following formula:

$$S = D \frac{W_{crystal} \sin\theta - W_{source}}{W_{crystal} \sin\theta + W_{detector}}$$

where D is the distance between the x-ray detector 150 and the crystal 162 of the x-ray analyzer 160 and is given by D=2R sin θ where R is the Rowland circle radius and θ is the Bragg angle, $W_{crystal}$ is the width of the crystal 162 of the x-ray analyzer 160, $W_{source}$ is the width of the illumination spot size on the sample 130, and $W_{detector}$ is the width of the pixel array of the x-ray detector 150.

For this position of the sample 130 relative to the x-ray analyzer 160, the pixel energy resolution can be expressed as:

$$\Delta E = E \cot\theta \frac{W_{pixel}}{2R\sin\theta}$$

and the energy coverage can be expressed as:

$$\Delta E = E \cot\theta \frac{W_{detector}}{2R\sin\theta},$$

where E is the energy of interest, θ is the Bragg angle, $W_{pixel}$ is the pixel width, $W_{detector}$ is the width of the pixel array of the x-ray detector 150, and 2R sin θ is the distance between the x-ray analyzer 160 and the x-ray detector 150 located on the Rowland circle 500. For example, for an x-ray detector 150 comprising a CCD pixel array with pixel size of 15 microns, a Rowland circle radius of 175 mm, a crystal width of 50 mm, an illumination spot size of 50 microns, and a Bragg angle of about 82 degrees for about 7 keV x-rays, the energy resolution can be estimated to be 0.04 eV. For a 50 eV coverage, the detector width is about 17.3 mm, so the distance between the illumination spot on the sample 130 and the x-ray analyzer 160 is about 256 mm, which corresponds to displacing the illumination spot by about 94 mm from the Rowland circle 500 towards the x-ray analyzer crystal 162. For a narrower energy coverage of 5 eV, the distance between the illumination spot on the sample 130 and the x-ray analyzer 160 is about 334 mm, which can be achieved by translating the illumination spot towards the Rowland circle 500 to a distance of about 16 mm from the Rowland circle 500. In certain embodiments, the location of the sample 130 relative to the Rowland circle 500 is controllably adjusted by translating the x-ray spectrometer relative to the sample 130, with the sample 130 remaining fixed in space.

Figure 9:
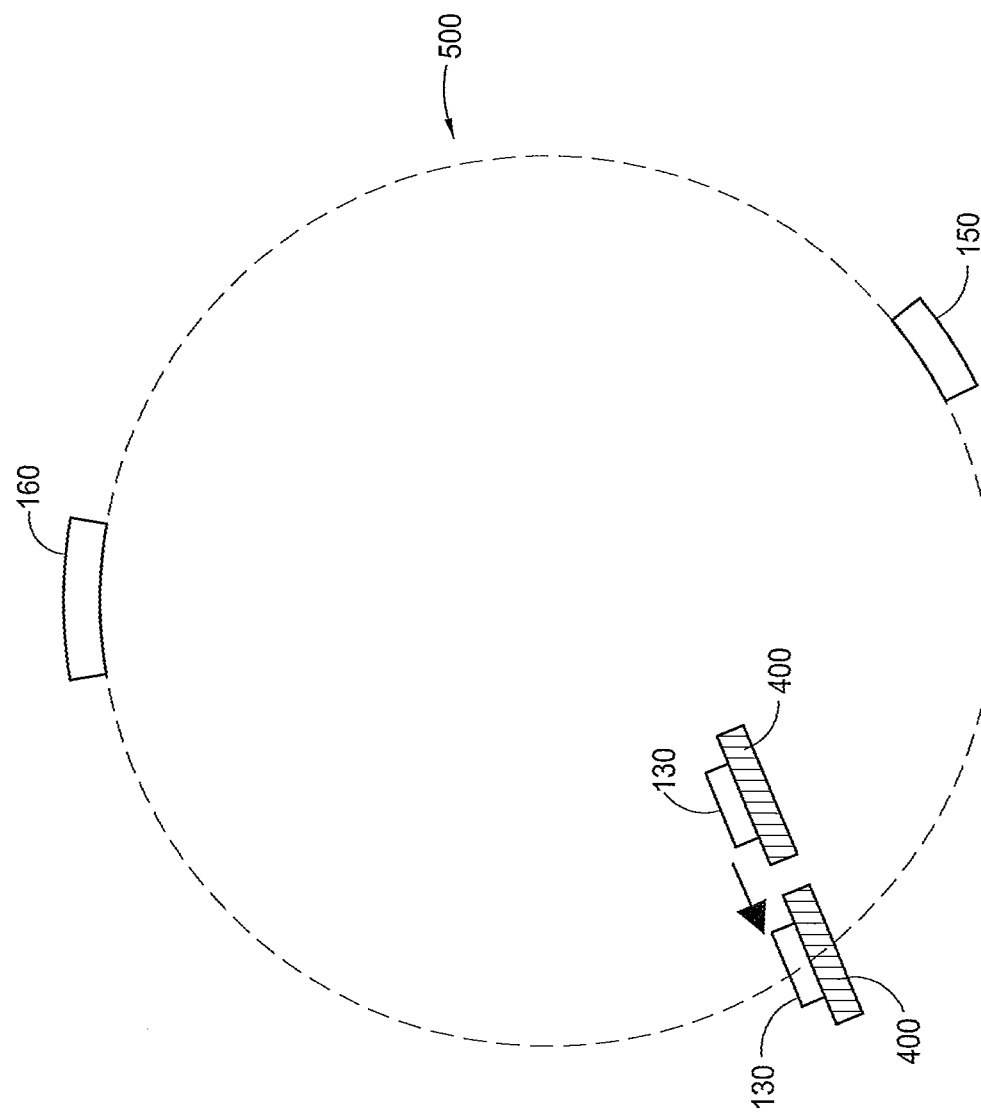
FIG. 9 schematically illustrates an example x-ray spectrometer system having a sample configured to move between a position off of the Rowland circle and a position on the Rowland circle in accordance with certain embodiments described herein.

FIG. 9 schematically illustrates an example x-ray spectrometer system 100 having a sample 130 configured to move between a position off of the Rowland circle 500 and a position on the Rowland circle 500 in accordance with certain embodiments described herein. In certain embodiments, the sample 130 moves from off the Rowland circle 500 to on the Rowland circle 500 during data acquisition (e.g., measurement and analysis of the fluorescence x-rays 410 from the sample 130), which can be performed to refine characterization of lower yield fluorescence x-ray lines, such x-ray lines corresponding to higher energy valence-to-core transitions.

Figure 10:
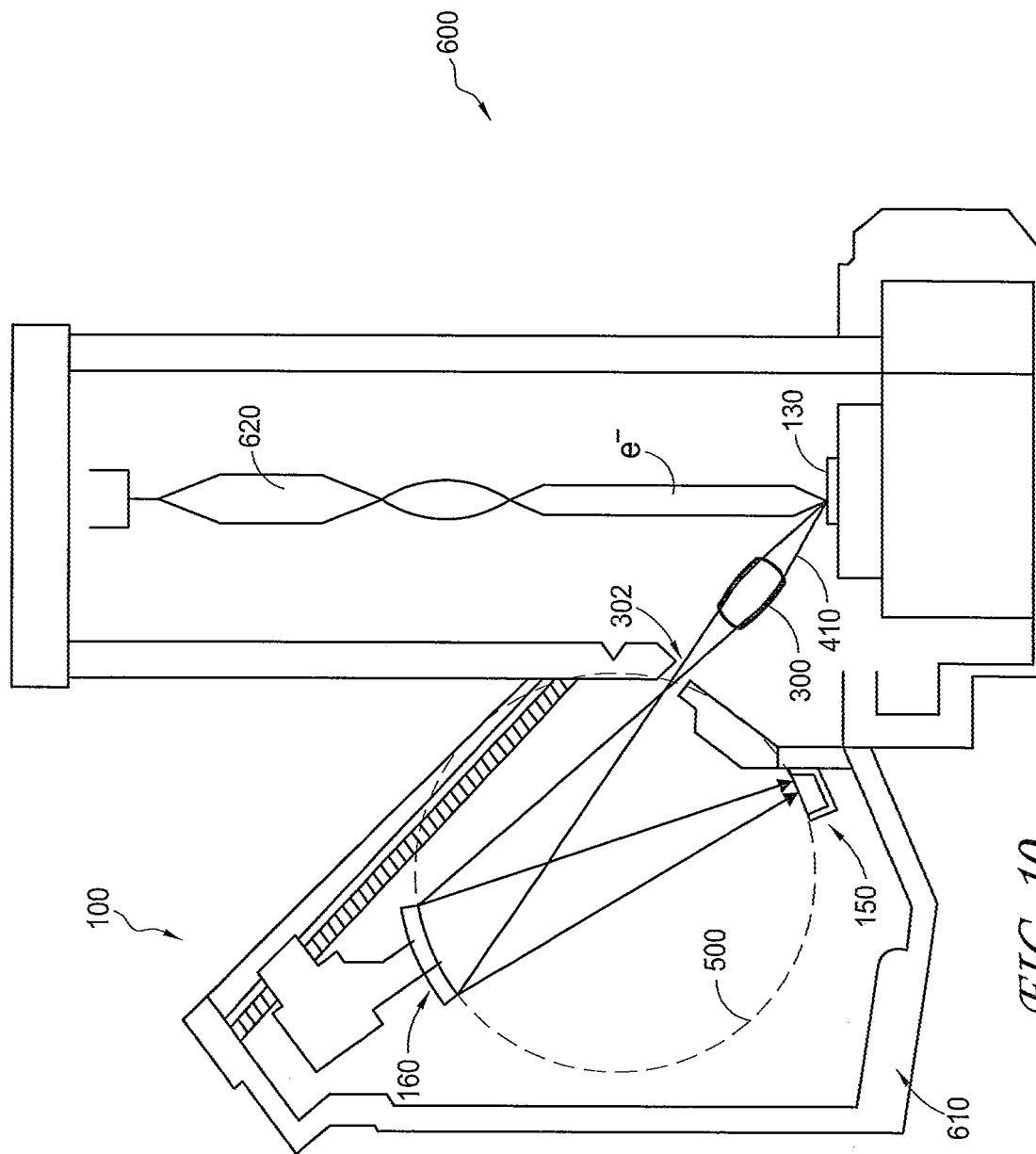
FIG. 10 schematically illustrates an example x-ray spectrometer system in conjunction with an electron microscope in accordance with certain embodiments described herein.

FIG. 10 schematically illustrates an example x-ray spectrometer system 100 in conjunction with an electron microscope 600 in accordance with certain embodiments described herein. In certain embodiments, the x-ray spectrometer system 100 is an attachment to the electron microscope 600 (e.g., scanning electron microscope (SEM); transmission electron microscope (TEM)), with a housing 610 configured to be reversibly attached to and detached from the electron microscope 600 (e.g., on a port of the electron microscope 600). In certain such embodiments, the electron beam 620 of the electron microscope 600 is focused on a sample 130 and the x-ray spectrometer system 100 is configured such that the focal spot 302 of the x-ray optical train 300, the x-ray analyzer 160, and the x-ray detector 150 each are on the Rowland circle 500 (e.g., an "on-Rowland circle" geometry). The focal spot 302 of the x-ray optical train 300 has a spot size (e.g., width; diameter) less than 500 microns (e.g., less than 200 microns; less than 100 microns; less than 50 microns).

In certain embodiments, the x-ray spectrometer system 100 is compact (e.g., having a Rowland circle radius less than or equal to 25 cm, less than or equal to 12.5 cm, or less than or equal to 10 cm), while in certain other embodiments, the Rowland circle radius is less than or equal to 75 cm. In certain embodiments, the x-ray spectrometer system 100 has the focal spot 302 and the x-ray detector 150 in proximity to one another (e.g., in a back-scatter geometry) and with Bragg angles θ of up to 90 degrees. In certain embodiments, the x-ray analyzer 160 is mounted on a stage 630 (e.g., comprising a linear motion motor and/or an adjustably rotatable mount) that is configured to translate the x-ray analyzer 160 such that the radius of the Rowland circle 500 can be controllably adjusted and/or to adjust an orientation of the x-ray analyzer 160 relative to the fluorescence x-rays 410 from the sample 130.

In certain embodiments, one or more of the sample 130, the x-ray analyzer 160, and the x-ray detector 150 of the x-ray spectrometer system 100 is enclosed in a vacuum chamber with pressures less than $10^{-5}$ torr. In certain embodiments, the x-ray spectrometer system 100 comprises one or more mounts (e.g., goniometers) or other mechanical mechanisms configured to tilt and/or move the sample 130 (e.g., mount 400), the x-ray analyzer 160 (e.g., stage 630), and/or the x-ray detector 150 so as to adjust the relative alignment of the x-ray origin (e.g., the focal spot 302), the x-ray analyzer 160, and the x-ray detector 150, as well as to adjust parameters of the Rowland circle (e.g., the radius of the Rowland circle 500). In certain embodiments, the x-ray spectroscopy system 100 is configured to be interchanged between multiple geometries (e.g., between "off-Rowland circle" geometry and "on-Rowland circle" geometry, between spherical Johannsson geometry and other geometries).

In certain embodiments, the focal spot size and x-ray detector resolution are configured such that the x-ray spectrometer system 100 is compact (e.g., the Rowland circle radius is less than or equal to 12.5 cm or less than or equal to 10 cm) while providing high energy resolution (e.g., less than 2 eV; less than 1 eV). For example, the energy resolving power of certain embodiments can reach 7000, which is equivalent to a spectral resolution of 0.25 eV, and certain embodiments described herein can achieve a spectral resolution better than 0.25 eV.

In certain embodiments, multiple x-ray generating materials and multiple x-ray optical trains 300 (e.g., matched to the x-ray generating materials) are used simultaneously to illuminate the sample 130 at a variety of angles for x-ray emission spectroscopy, which can significantly improve throughput for applications such as production environments.

Figure 11:
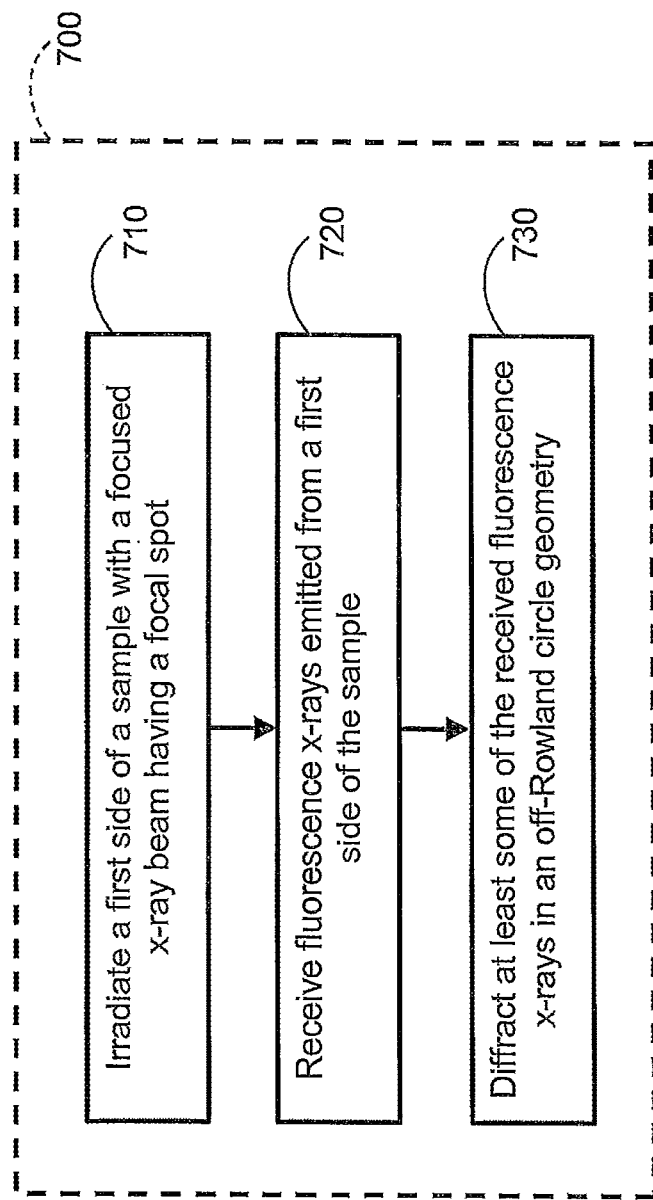
FIG. 11 is a flow diagram of an example method for x-ray emission spectroscopy in accordance with certain embodiments described herein.

FIG. 11 is a flow diagram of an example method 700 for x-ray emission spectroscopy in accordance with certain embodiments described herein. In an operational block, 710, the method 700 comprises irradiating a first side of a sample 130 with a focused x-ray beam 320 having a focal spot 302.

In an operational block 720, the method 700 further comprises receiving fluorescence x-rays 410 emitted from the first side of the sample 130. In an operational block 730, the method 700 further comprises diffracting, using at least one x-ray analyzer 160, at least some of the received fluorescence x-rays 410 such that fluorescence x-rays with different wavelengths are diffracted towards different portions of at least one spatially-resolving x-ray detector 150. The focal spot 302, the at least one x-ray analyzer 160, and the at least one spatially-resolving x-ray detector 150 are positioned in an off-Rowland circle geometry.

Figure 12:
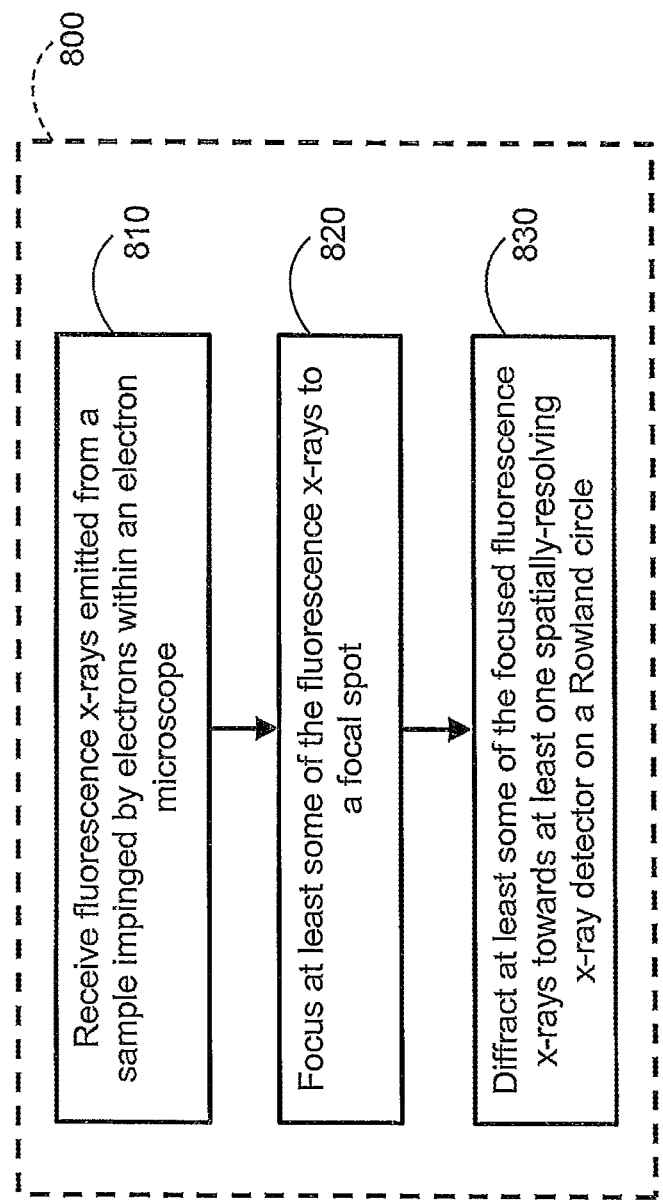
FIG. 12 is a flow diagram of another example method for x-ray emission spectroscopy in accordance with certain embodiments described herein.

FIG. 12 is a flow diagram of another example method 800 for x-ray emission spectroscopy in accordance with certain embodiments described herein. In an operational block 810, the method 800 comprises receiving fluorescence x-rays 410 emitted from a sample 130 impinged by electrons 620 within an electron microscope 600. In an operational block 820, the method 800 further comprises focusing at least some of the received fluorescence x-rays 410 to a focal spot 302. In an operational block 830, the method 800 further comprises diffracting, using at least one x-ray analyzer 160, at least some of the focused fluorescence x-rays such that fluorescence x-rays with different wavelengths are diffracted towards different portions of at least one spatially-resolving x-ray detector 150. The at least one x-ray analyzer 160 and the at least one spatially-resolving x-ray detector 150 are positioned on a Rowland circle 500. In certain embodiments, the method 800 further comprises controllably adjusting the Rowland circle 500 relative to the focal spot 302 while the sample 130 remains stationary such that the focal spot 302 is selected to be at a first position on the Rowland circle 500 or a second position off the Rowland circle 500.

Various configurations have been described above. Although this invention has been described with reference to these specific configurations, the descriptions are intended to be illustrative of the invention and are not intended to be limiting. Various modifications and applications may occur to those skilled in the art without departing from the true spirit and scope of the invention. Thus, for example, in any method or process disclosed herein, the acts or operations making up the method/process may be performed in any suitable sequence and are not necessarily limited to any particular disclosed sequence. Features or elements from various embodiments and examples discussed above may be combined with one another to produce alternative configurations compatible with embodiments disclosed herein. Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

What is claimed is:

1. A system for x-ray emission spectroscopy, the system comprising:
   a mount configured to hold a sample;
   at least one x-ray source;
   at least one x-ray optical train configured to focus x-rays from the at least one x-ray source to a focal spot and to irradiate a first side of the sample with the focused x-rays;
   at least one x-ray analyzer curved in at least one plane, the at least one x-ray analyzer configured to receive fluorescence x-rays emitted from the first side of the sample; and
   at least one spatially-resolving x-ray detector, wherein the focal spot, the at least one x-ray analyzer, and the at least one spatially-resolving x-ray detector are positioned in an off-Rowland circle geometry.

2. The system of claim 1, wherein at least one x-ray optical train comprises at least one capillary x-ray optic comprising an x-ray reflecting portion with a surface profile in the form of a portion of a quadric surface.

3. The system of claim 1, wherein the at least one x-ray source comprises at least one electron beam emitter configured to generate at least one electron beam and at least one target comprising a plurality of x-ray generating structures configured to generate x-rays having a characteristic x-ray spectrum in response to being irradiated by the at least one electron beam.

4. The system of claim 3, wherein the at least one x-ray optical train comprises a plurality of x-ray optical trains configured to be interchanged with one another, each x-ray optical train of the plurality of x-ray optical trains matched to at least one x-ray generating structure of the plurality of x-ray generating structures.

5. The system of claim 1, wherein the at least one x-ray analyzer comprises at least one doubly curved single crystal or mosaic crystal.

6. The system of claim 1, wherein the at least one x-ray analyzer comprises a Wittry crystal.

7. The system of claim 1, wherein the at least one x-ray analyzer comprises a plurality of x-ray analyzers that are configured to be interchanged with one another.

8. The system of claim 1, wherein the at least one spatially-resolving x-ray detector comprises a charge coupled device (CCD) detector with pixel widths smaller than 20 microns.

9. The system of claim 1, wherein a Rowland circle of the system has a radius less than or equal to 12.5 cm.

10. The system of claim 1, wherein the focal spot has a width less than 100 microns.

11. The system of claim 1, wherein the at least one x-ray optical train has a reflectivity with a predetermined cut-off energy such that the reflectivity for x-rays having energies greater than 1.2 times the cut-off energy is below 25%.

12. The system of claim 1, wherein the at least one x-ray analyzer comprises a single crystal or a mosaic crystal and the at least one plane comprises a dispersion plane.

13. An x-ray spectrometer comprising:
   at least one x-ray optical train configured to receive fluorescence x-rays emitted from a sample impinged by electrons within an electron microscope and to focus at least some of the received fluorescence x-rays to a focal spot;
   at least one spatially-resolving x-ray detector; and
   at least one x-ray analyzer curved in at least one plane, the at least one x-ray analyzer configured to receive and diffract at least some of the focused fluorescence x-rays with x-rays of different wavelengths diffracted to different locations on the at least one spatially-resolving x-ray detector, wherein the at least one x-ray analyzer and the at least one spatially-resolving x-ray detector are positioned on a Rowland circle.

14. The x-ray spectrometer of claim 13, wherein the at least one x-ray optical train has a focal spot with a width less than or equal to 50 microns.

15. The x-ray spectrometer of claim 13, wherein the at least one x-ray analyzer comprises a doubly curved single crystal or mosaic crystal.

16. The x-ray spectrometer of claim 13, wherein the at least one x-ray optical train comprises a capillary x-ray optic capillary x-ray optic comprising an x-ray reflecting portion with a surface profile in the form of a portion of a quadric surface.

17. The x-ray spectrometer of claim 13, wherein the at least one optical train has a working distance of greater than 10 mm at the focal spot.

18. The x-ray spectrometer of claim 13, wherein the system is configured to be reversibly attached to and detached from the electron microscope.

19. The x-ray spectrometer of claim 13, wherein the Rowland circle is configured to be controllably adjusted relative to the focal spot while the sample remains stationary such that the focal spot is selected to be at a first position on the Rowland circle or a second position off the Rowland circle.

20. A method for x-ray emission spectroscopy, the method comprising:
    irradiating a first side of a sample with a focused x-ray beam having a focal spot;
    receiving fluorescence x-rays emitted from the first side of the sample; and
    diffracting, using at least one x-ray analyzer, at least some of the received fluorescence x-rays such that fluorescence x-rays with different wavelengths are diffracted towards different portions of at least one spatially-resolving x-ray detector, wherein the focal spot, the at least one x-ray analyzer, and the at least one spatially-resolving x-ray detector are positioned in an off-Rowland circle geometry.

21. A method for x-ray emission spectroscopy, the method comprising:
    receiving fluorescence x-rays emitted from a sample impinged by electrons within an electron microscope;
    focusing at least some of the received fluorescence x-rays to a focal spot; and
    diffracting, using at least one x-ray analyzer, at least some of the focused fluorescence x-rays such that fluorescence x-rays with different wavelengths are diffracted towards different portions of at least one spatially-resolving x-ray detector;
    wherein the at least one x-ray analyzer and the at least one spatially-resolving x-ray detector are positioned on a Rowland circle.

22. The method of claim 21, further comprising controllably adjusting the Rowland circle relative to the focal spot while the sample remains stationary such that the focal spot is selected to be at a first position on the Rowland circle or a second position off the Rowland circle.

* * * * *

UNITED STATES PATENT AND TRADEMARK OFFICE
CERTIFICATE OF CORRECTION

PATENT NO. : 10,578,566 B2  
APPLICATION NO. : 16/371606  
DATED : March 3, 2020  
INVENTOR(S) : Wenbing Yun Page 1 of 1

It is certified that error appears in the above-identified patent and that said Letters Patent is hereby corrected as shown below:

In the Specification

Column 8, Line 5, delete "we" and insert --$w_c$--.

Column 8, Line 6, delete "w," and insert --$w_s$--.

Column 8, Line 7, delete "we" and insert --$w_c$--.

Column 12, Line 45, delete "$\mu_N$" and insert --$\lambda_N$--.

Signed and Sealed this  
Twenty-eighth Day of July, 2020

Andrei Iancu  
*Director of the United States Patent and Trademark Office*